US009028872B2

(12) United States Patent
Gaserod et al.

(10) Patent No.: US 9,028,872 B2
(45) Date of Patent: May 12, 2015

(54) GELLED COMPOSITE

(75) Inventors: Olav Gaserod, Steinberg (NO); Therese Andersen, Sande I Vestford (NO); Jan Egil Melvik, Oslo (NO); Michael Dornish, Bekkestua (NO); Peter J. Riley, Yardley, PA (US)

(73) Assignee: FMC Corporation, Philadelphia, PA (US)

( * ) Notice: Subject to any disclaimer, the term of this patent is extended or adjusted under 35 U.S.C. 154(b) by 865 days.

(21) Appl. No.: 11/712,612

(22) Filed: Mar. 1, 2007

(65) Prior Publication Data

US 2008/0033392 A1 Feb. 7, 2008

Related U.S. Application Data

(60) Provisional application No. 60/777,869, filed on Mar. 1, 2006, provisional application No. 60/872,844, filed on Dec. 5, 2006, provisional application No. 60/874,174, filed on Dec. 11, 2006.

(51) Int. Cl.
| A61K 9/70 | (2006.01) |
| A61L 27/56 | (2006.01) |
| A61K 9/12 | (2006.01) |
| A61K 47/36 | (2006.01) |
| A61L 27/20 | (2006.01) |
| A61L 27/38 | (2006.01) |
| A61L 27/48 | (2006.01) |

(52) U.S. Cl.
CPC ............... *A61L 27/56* (2013.01); *A61K 9/122* (2013.01); *A61K 47/36* (2013.01); *A61L 27/20* (2013.01); *A61L 27/38* (2013.01); *A61L 27/48* (2013.01)

(58) Field of Classification Search
CPC .................................................. A61K 9/0014
See application file for complete search history.

(56) References Cited

U.S. PATENT DOCUMENTS

| 2,036,934 | A | | 4/1936 | Green |
| 2,128,551 | A | | 3/1938 | Le Gloahec et al. |
| 2,426,125 | A | | 8/1947 | Steiner |
| 3,772,266 | A | | 11/1973 | Pettitt et al. |
| 3,929,678 | A | | 12/1975 | Laughlin et al. |
| 3,948,881 | A | | 4/1976 | Strong |
| 4,292,972 | A | | 10/1981 | Pawelchak et al. |
| 4,948,575 | A | | 8/1990 | Cole et al. |
| 5,709,934 | A | | 1/1998 | Bell et al. |
| 5,735,902 | A | | 4/1998 | Li et al. |
| 5,756,111 | A | | 5/1998 | Yoshikawa et al. |
| 5,830,493 | A | | 11/1998 | Yokota et al. |
| 5,840,777 | A | * | 11/1998 | Eagles et al. ............ 521/82 |
| 5,851,461 | A | | 12/1998 | Bakis et al. |
| 5,888,987 | A | | 3/1999 | Hayes |
| 5,948,429 | A | | 9/1999 | Bell et al. |
| 6,054,142 | A | | 4/2000 | Li et al. |
| 6,153,292 | A | | 11/2000 | Bell et al. |
| 6,203,845 | B1 | | 3/2001 | Qin et al. |
| 6,231,879 | B1 | | 5/2001 | Li et al. |
| 6,281,256 | B1 | | 8/2001 | Harris et al. |
| 6,294,202 | B1 | | 9/2001 | Burns et al. |
| 6,306,169 | B1 | * | 10/2001 | Lee et al. ............ 623/11.11 |
| 6,334,968 | B1 | | 1/2002 | Shapiro et al. |
| 6,425,918 | B1 | | 7/2002 | Shapiro et al. |
| 6,565,960 | B2 | | 5/2003 | Koob et al. |
| 6,589,328 | B1 | | 7/2003 | Nussinovitch |
| 6,630,167 | B2 | | 10/2003 | Zhang et al. |
| 6,642,363 | B1 | | 11/2003 | Mooney et al. |
| 6,656,974 | B1 | | 12/2003 | Renn et al. |
| 6,730,298 | B2 | | 5/2004 | Griffith-Cima |
| 6,793,675 | B2 | | 9/2004 | Shapiro et al. |
| 6,797,738 | B2 | | 9/2004 | Harris et al. |
| 6,821,530 | B2 | | 11/2004 | Koob et al. |
| 6,855,860 | B2 | | 2/2005 | Ruszczak et al. |
| 6,960,617 | B2 | | 11/2005 | Omidian et al. |
| 2002/0001610 | A1 | | 1/2002 | Cohen et al. |
| 2002/0111576 | A1 | | 8/2002 | Green et al. |
| 2003/0021832 | A1 | | 1/2003 | Scherr |
| 2003/0224022 | A1 | | 12/2003 | Nussinovitch |
| 2004/0071776 | A1 | * | 4/2004 | Boudy et al. ............ 424/486 |
| 2004/0082063 | A1 | | 4/2004 | Deshpande et al. |

(Continued)

FOREIGN PATENT DOCUMENTS

| CN | 1587306 | 4/1999 |
| CN | 1820789 | 8/2006 |

(Continued)

OTHER PUBLICATIONS

International Search Report and Written Opinion of the International Searching Authority—International Application No. PCT/us2007/0054326—International Filing Date Jan. 3, 2007.
Partial International Search Report—International Application No. PCT/US2007/005436—International Filing Date—Jan. 3, 2007.
von Heimburg et al., "Influence of different biodegradable carriers on the in vivo behavior of human adipose precursor cells." Plast Reconstr Surg. Aug. 2001; 108(2), pp. 411-420, discussion 421-2. (Abstract only).
Zavan B. et al., "Extracellular matrix-enriched polymeric scaffolds as a substrate for hepatocyte cultures: in vitro and in vivo studies." Biomaterials 26 (2005) pp. 7038-7045.

(Continued)

*Primary Examiner* — Tigabu Kassa
(74) *Attorney, Agent, or Firm* — FMC Corporation

(57) ABSTRACT

The invention relates to composites comprising a polysaccharide gelled within pores of a foam, methods of preparation, and uses thereof, for example, in biomedical applications such as cell culture media and implants, controlled release delivery systems, food applications, industrial applications, and personal care applications such as cosmetic and oral hygiene. The composites of the present invention are simple to formulate using few steps and are useful for entrapping heat-sensitive components, such as cells, drugs, flavors or fragrances within the polysaccharide gel. In addition, the invention provides for a composite able to gently immobilize fragile components, such as living cells, without exposing such components to shear forces.

7 Claims, No Drawings

(56) References Cited

U.S. PATENT DOCUMENTS

| | | |
|---|---|---|
| 2004/0243043 A1 | 12/2004 | McCarthy et al. |
| 2005/0038369 A1 | 2/2005 | Gregory et al. |
| 2005/0137272 A1 | 6/2005 | Gaserod et al. |
| 2005/0137512 A1 | 6/2005 | Campbell et al. |
| 2005/0147656 A1 | 7/2005 | McCarthy et al. |
| 2005/0148963 A1 | 7/2005 | Brennan |
| 2005/0169895 A1 | 8/2005 | Melvik |
| 2006/0004314 A1 | 1/2006 | McCarthy et al. |
| 2006/0153814 A1 | 7/2006 | Liao et al. |
| 2006/0159823 A1 | 7/2006 | Melvik et al. |
| 2006/0240080 A1 | 10/2006 | Han et al. |
| 2007/0249044 A1 | 10/2007 | Desai et al. |
| 2008/0044900 A1 | 2/2008 | Mooney et al. |
| 2008/0145344 A1 | 6/2008 | Deshpande et al. |

FOREIGN PATENT DOCUMENTS

| | | |
|---|---|---|
| EP | 0 537 999 A2 | 4/1993 |
| EP | 0 747 420 A1 | 12/1996 |
| EP | 1127914 A2 | 8/2001 |
| GB | 1570485 | 7/1980 |
| JP | 2001-278984 | 10/2001 |
| JP | 2002-105233 | 4/2002 |
| WO | WO 00/16817 | 3/2000 |
| WO | WO-01/54735 A2 | 8/2001 |
| WO | WO-0154735 A2 | 8/2001 |
| WO | 03037282 A1 | 5/2003 |
| WO | 03037294 A2 | 5/2003 |
| WO | WO-2005023323 A1 | 3/2005 |

OTHER PUBLICATIONS

Park, Yoon Jeong et al., "Platelet derived growth factor releasing chitosan sponge for periodontal bone regeneration." Biomaterials 21 (2000) pp. 153-159.

Halblieb et al., "Tissue engineering of white adipose tissue using hyaluronic acid-based scaffolds. I: in vitro differentiation of human adipocyte precursor cells on scaffolds." Biomaterials, Aug. 2003; 24(18), pp. 3125-3132. (Abstract only).

Hemmrich et al., "Implantation of preadipocyte-loaded hyaluronic acid-based scaffolds into nude mice to evaluate potential for soft tissue engineering." Biomaterials, Dec. 2005; 26(34), pp. 7025-7027. (Abstract only).

Solchaga et al., "Hyaluronic acid-based polymers as cell carriers for tissue-engineered repair of bone and cartilage." J Orthop Res. Mar. 1999; 17(2), pp. 205-213. (Abstract only).

J. Berger, et al. Article, "Structure and interactions in covalently and ionically crosslinked chitosan hydrogels for biomedical applications", European Journal of Pharmaceutics and Biopharmaceutics 57 (2004) 19-34.

\* cited by examiner

GELLED COMPOSITE

This application claims the benefit of U.S. Provisional Application No. 60/777,869, filed Mar. 1, 2006; U.S. Provisional Application No. 60/872,844, filed Dec. 5, 2006; and U.S. Provisional Application No. 60/874,174, filed Dec. 11, 2006.

The invention relates to a composite comprising a polysaccharide gelled within pores of a foam, methods of preparation of the composite, and uses thereof. The composite is particularly useful in biomedical applications for example cell culture media and implants, controlled release delivery systems, food applications, industrial applications, and personal care applications including cosmetic and oral hygiene.

U.S. Pat. No. 5,948,429 (Bell) discloses methods for preparing coated biopolymer foams including cross-linking biopolymer foams by ultraviolet radiation, optionally washing with sterile buffer followed by deionized water to increase tensile strength, and then coating with an uncross-linked collagen.

WO0154735 A2 (Bentz) discloses gel infused sponges where a gel precursor comprised of a protein solution or modified polysaccharide and a cross-linking agent, if required, is typically added to a sponge prior to its transition to solid gel consistency. Gel initiation can be triggered enzymatically, thermally, photo-chemically, or chemically. Here, however, the gel forming agent is not integrated into the foam matrix but added to the matrix.

U.S. Pat. No. 6,306,169 (Lee) discloses a biomechanical implant comprising two matrix components, one being a collagen implant and the other a hydrated alginate gel which exerts a swelling pressure. The implant comprises a population of cells. In making the composite, a sodium alginate solution may be caused to swell by immersion in a saline solution to create tensile forces between the alginate and collagen matrix. The composite construct can then be immersed in a solution containing a salt of a divalent cation to induce cross-linkage of the alginate to form a hydrated gel.

U.S. Pat. No. 6,203,845 (Qin) discloses a method to form a dehydrated (porous) hydrogel by dispensing cation-containing fibers into an aqueous solution of a hydrogel precursor incorporating a plasticizer to form a hydrogel and then dehydrating the hydrogel.

U.S. Pat. No. 6,656,974 (Renn) discloses an absorbent foam material comprising a solid cross-linked form of an anionic polymer and fibers or other polymeric particulates which have donated cations to effect cross-linking of the anionic polymer. The fibers remain in the final foam to act as reinforcement. There is no suggestion that the final foam is further reacted to produce a further product nor that the foam contains further cations suitable for donation to further reactants.

A need remains to provide a product suitable for use for example in wound management, tissue engineering, tissue regeneration and cell immobilization. The present inventors have found that a composite possessing an excellent combination of characteristics may be produced by forming a composite comprising a foam having pores and a gel formed in situ within the pores of the foam.

In one aspect, the invention provides a method for forming a composite comprising a foam and a gel formed in situ within the pores of the foam, the method comprising providing a foam having pores and which foam comprises a polymer, preferably a cross-linkable polymer, and gel-forming ions for forming a gel, contacting a liquid component with the said foam, said liquid component comprising a soluble polysaccharide having gelling sites capable of forming a gel upon contact with the said gel-forming ions, whereby upon contact with the said ions, a gel comprising the soluble polysaccharide is formed within the pores of the said foam.

Advantageously, the gel in the composite has good structural integrity for its intended use, for example the gel does not leak from the foam unless desired. The composite has an excellent combination of physical characteristics as compared to known hydrogels and the composite may be employed to carry functional components, for example pharmaceuticals and cell populations and provides desirable delivery characteristics, for example release of the material to be released. The release may be triggered in any suitable manner, for example by contact with a solvent, by temperature change or by mechanical manipulation. The composite may advantageously be employed to immobilize cells.

The composite may be produced by an in situ method in which the foam is employed in its intended location and then the soluble polysaccharide is added to the foam so as to form the composite in situ. The foam may be shaped prior to or during use as desired. The foam may be secured to a substrate with a fastener, for example a suture, and the soluble polysaccharide then added to the foam to produce the gel and form the composite. As desired. the composite may be formed and then secured to a substrate using a fastener, for example a suture.

Temperature-sensitive materials may suitably be incorporated in the composite as the composite is suitably formed by a process at or near to ambient temperature. The method of the invention does not need to include a drying step at elevated or reduced temperature for example a freeze drying step although this may be included if desired. The option to avoid drying the composite, especially at elevated temperature, advantageously allows the production of a composite in which the incorporated temperature-sensitive material may be evenly distributed and not deactivated or altered.

The method suitably includes absorbing a liquid component containing a polysaccharide into a foam having pores where gel-forming ions are incorporated in the foam, and gelling the polysaccharide within pores of the foam. The polysaccharide in the liquid component is suitably reactive with the gel-forming ions in the foam so as to form the gel.

In a third aspect, the invention is directed towards a composite produced by the method of the invention.

In a further aspect, the invention provides for the use of a composite produced according to the method of the invention.

The composite comprises a gel formed in situ within the foam structure and the gel is dispersed within the foam. The composite is particularly suitable for use in medical applications, for example in wound management, tissue engineering and tissue regeneration and cell immobilization.

Suitably, the composite has a physiologically compatible pH. The foam or the gel may be degradable and both are preferably degradable. The foam and gel may be degradable under the same or differing conditions or at different rates or times within the human or animal body.

The composite comprising a polysaccharide gel formed in situ within the pores of the foam is prepared by adding a liquid component containing a polysaccharide to a foam which has pores and gel-forming ions incorporated within the foam thereby inducing gelling of the polysaccharide.

Suitable foams include those having open pore networks preferably having a pore size from 5 to 1000 microns, more preferably in the range of 25 to 500 microns, capable of absorbing an added liquid component containing a polysaccharide into its pores. Suitable foams for use in the present invention have pores open on at least one surface and desirably have at least a portion of interconnected pores to enable transport of the absorbed polysaccharide within the foam and/or effectively increase the volume of liquid component which can be absorbed suitably by the foam.

The foam is suitably swellable and preferably may absorb up to 30 times its weight, more preferably from 1 to 20 times its weight of a liquid, for example an aqueous physiological solution or a polysaccharide solution. The foam can have a homogeneous or heterogenous distribution of pore sizes. Not all pores are required to absorb the liquid component.

Suitably, the foam, the composite or a device containing the composite is sterilized, preferably by γ-irradiation, E-beam, ethylene oxide, autoclaving or contacting the foam with alcohol prior to addition of the liquid component or contacting with NOx gases, hydrogen gas plasma sterilization. Sterilisation should not be employed where it adversely affects the composite, or a functional component contained in the composite.

The polymer in the foam may be ionically or covalently cross-linkable but does not need to be cross-linkable provided that the soluble polysaccharide is cross-linkable with the polymer in the foam or with a component of the foam, for example the gel-forming ions.

In a preferred embodiment, the foams are formed from biopolymers which are derived from plants or animals. Such foams can be made according to prior art processes, for example, as disclosed in U.S. Pat. No. 5,888,987 (Hayes) or WO2005023323 (Gaserod), U.S. Pat. No. 6,203,845 (Qin) or U.S. Pat. No. 6,656,974 (Renn).

The gel-forming ions in the foam are present in sufficient quantity to form a gel with at least a portion of the polysaccharide.

Gel-forming ions for reacting with the liquid component comprising the polysaccharide may be incorporated during preparation of the foam or added to the foam preferably prior to addition of the liquid component. The gel-forming ions may be incorporated by being dispersed within a mixture, preferably a biopolymer mixture, prior to formation of the mixture into a wet foam or added to the formed foam. Optionally, additional gel-forming ions may be added to the composite comprising a foam and the gel comprising the added polysaccharide. Gel-forming ions may be incorporated into the foam or mixture for making the foam for example, by washing or soaking the foam with a gelling ion solution which does not dissolve the foam. Excess solution may be removed by compressing.

By providing sufficient gel-forming ions in the foam prior to the addition of the liquid component comprising the polysaccharide a composite having a gel formed through at least a part of the volume of the composite may be secured.

In a further aspect, the invention provides a composite comprising a foam, preferably a foam comprising a biopolymer, wherein the foam has pores and comprises gel-forming ions distributed, preferably substantially uniformly distributed, through the foam and a gel comprising a polysaccharide wherein the gel is located within the pores of the foam and interacts with the foam.

Preferably the gel-forming ions are present in at least some of the internal pores of the foam rather than only surface pores. The gel-forming ions are preferably substantially evenly distributed in the foam. By providing gel-forming ions in the foam prior to introduction of the liquid component comprising a polysaccharide, the polysaccharide may interact with the ions such that on addition of the liquid component comprising the polysaccharide, a gel forms in at least part of and preferably through substantially all of the internal volume of the foam.

The interaction between the gel and the foam may be chemical through bonding between the foam and the polysaccharide by means of the gel-forming ions forming "bridges". The interaction may be physical through the gel being retained in the pores of the foam by physical interlocking of the gel and foam.

The foam comprises the gel-forming ions and upon addition of the liquid containing the polysaccharide, the polysaccharide may advantageously penetrate to the interior of the foam via pores and channels in the foam and react with the gel-forming ions so as to form the composite. In this way the gel is formed through at least a part of the interior volume of the foam. Addition of the polysaccharide to the foam before incorporating the gel-forming ions is disadvantageous in that on adding the said ions, reaction is likely to take place on or near the surface of the foam so forming a gel layer which may impede penetration of said ions to the interior volume of the foam. Furthermore, the gel and the composite may be undesirably inhomogeneous.

In a preferred embodiment, the composite comprises a substantially homogeneous gel.

In one embodiment, the polymer used for the foam matrix comprises a polysaccharide which is gelled with gel-forming ions. In a preferred embodiment the foam comprises a crosslinked biopolymer optionally containing a foaming agent for example as described in WO2005023323.

The foam preferably comprises a polysaccharide and/or a chemically modified polysaccharide. Modified polysaccharides for example peptide-coupled polysaccharides are prepared by means known in the art. For example, modified alginates are disclosed in U.S. Pat. No. 6,642,363 (Mooney). Peptide-coupled polysaccharides are preferred for use for example in immobilizing cells to promote cell proliferation and cell differentiation. Peptide-coupled polysaccharides are preferably employed in combination with non-modified polysaccharides.

The foam is preferably dried absorbent foam.

In a preferred embodiment the invention provides a method for forming a dried absorbent foam having an open pore network and pores and comprising gel-forming ions for gelling a subsequently added polysaccharide solution which method comprises:

a) forming a wet foam from an aqueous dispersion comprising a polysaccharide, and a foaming agent and optionally one or more of a plasticizer, a cross-linking agent and a pH modifier;

b) mixing a foam from the aqueous dispersion, optionally by mechanical agitation;

c) optionally carrying out one or more steps of:
  i) molding or shaping the foam; and
  ii) forming a cross-linked foam from the foam;

d) drying the foam to form a dried foam containing open pores; and e) adding gel-forming ions in one or more of steps a) to d) or after step d).

In an especially preferred embodiment, the gel-forming ions are added in step a) to provide a substantially uniform distribution of the said gel-forming ions throughout the foam.

Known pH modifiers to reduce or increase pH and plasticizers may be employed for example, those described in WO2005023323.

The foam may be dried by air drying and as desired may be subjected to molding, shaping or compression.

The foam used in the present invention is preferably a polysaccharide. Examples of suitable polysaccharides for producing the foam include alginates, pectins, carrageenans, hyaluronates, chitosan and mixtures thereof. Alginates, chitosan and hyaluronates are preferred polysaccharides.

The foam may be prepared using a single foam preferably or alternatively from a heterogenous structure comprising foams of differing density or pore size, and foam and non-foam regions.

Suitable polysaccharides for use in the present invention include those that are soluble in a solvent, such as water, and can be formed into a gel by interaction with gel-forming ions. Examples of suitable polysaccharides include alginates, pectins, carrageenans, chitosan, hyaluronates, and mixtures thereof provided that the polysaccharide alone or in a mixture with another polysaccharide may form a gel. Alginates are a preferred polysaccharide for use in the present invention.

Alginates are salts of alginic acid. Alginic acid, which is isolated from seaweed, is a polyuronic acid made up of two uronic acids: D-mannuronic acid and L-guluronic acid. The ratio of mannuronic acid and guluronic acid varies with factors such as seaweed species, plant age, and part of the seaweed (e.g., stem, leaf). Alginic acid is substantially insoluble in water. It forms water-soluble salts with alkali metals, such as sodium, potassium, and, lithium; magnesium; ammonium; and the substituted ammonium cations derived from lower amines, such as methyl amine, ethanol amine, diethanol amine, and triethanol amine. The salts are soluble in aqueous media above pH 4, but are converted to alginic acid when the pH is lowered below about pH 4. A thermo-irreversible water-insoluble alginate gel is formed in the presence of gel-forming ions, e.g. calcium, barium, strontium, zinc, copper(+2), aluminum, and mixtures thereof, at appropriate concentrations. The alginate gels can be solubilized by soaking in a solution of soluble cations or chelating agents for the gel-forming ions, for example EDTA, citrate and the like.

Water-insoluble alginate salts, in which the principal cation is calcium are found in the fronds and stems of seaweeds of the class Phaeophyceae, examples of which are *Fucus vesiculosus, Fucus spiralis, Ascophyllum nodosum, Macrocystis pyrifera, Alaria esculenta, Eclonia maxima, Lessonia nigrescens, Lessonia trabeculata, Laminaria japonica, Durvillea antarctica, Laminaria hyperborea, Laminaria longicruris, Laminaria digitata, Laminaria saccharina, Laminaria cloustoni*, and *Saragassum* sp. Methods for the recovery of alginic acid and its water-soluble salts, especially sodium alginate, from natural sources are well known, and are described, for example, in Green, U.S. Pat. No. 2,036,934, and Le Gloahec, U.S. Pat. No. 2,128,551.

In a further embodiment, the polymer comprises chitosan. Chitosan is a linear polysaccharide comprising β-(1→4)-linked 2-acetamido-2-dexoy-D-glucopyranose (GlcNAc) and 2-amino-2-deoxy-D-glucopyranose (GlcN). Chitosan is N-deacetylated derivative of chitin, which consists nearly entirely of β-(1→4)-linked 2-acetamido-2-dexoy-D-glucopyranose (GlcNAc). Commercially chitosan is made by alkaline N-deacetylation of chitin. The heterogeneous deacetylation process combined with removal of insoluble compound results in a chitosan product which possesses a random distribution of GlcNAc and GlcN— units along the polymer chain. The amino group in chitosan has an apparent $pK_a$-value of about 6.5 and at a pH below this value, the free amino group will be protonized so the chitosan salt dissolved in solution will carry a positive charge. Accordingly, chitosan is able to react with negatively charged components it being a direct function of the positive charge density of chitosan.

Advantageously, the cationic nature of chitosan provides a bioadhesive property. In addition, chitosan may precipitate red blood cells due to their negative charge providing benefits in forming blood clots and in reducing the level of fibrin during healing so reducing the formation of scar tissue. Chitosan may be degraded by lysozyme and other related enzymes occurring in a mammalian body, for example the human body. In use the chitosan in a foam of the present invention will suitably be degraded by lysozyme found in mammals in saliva, tears, blood serum and in interstitial fluid. A composite having a chitosan foam may advantageously be employed in wound management, as a bioadhesive and in other applications in the human or animal body. Enzymatic degradation allows the foam to be designed in such a manner that the product may perform its function and then be removed from the body through degradation.

Pectin is a naturally occurring polysaccharide found in the roots, stems, leaves, and fruits of various plants, especially the peel of citrus fruits such as limes, lemons, grapefruits, and oranges. Pectins contain polymeric units derived from D-galacturonic acid. Commercial products include high methoxy pectin and low methoxy pectin (and derivatives such as amidated pectins). where 20-60% of the units derived from D-galacturonic acid, depending on the source of the pectin, are esterified with methyl groups. Pectate (pectinate) is fully de-esterified pectin with up to 20% of the units derived from D-galacturonic acid.

Carrageenan refers to a group of sulfated galactans which may be extracted from red seaweeds. Carrageenans are linear chains of D-galactopyranosyl units joined with alternating (1→3) α-D and (1→4) β-D-glycosidic linkages. Carrageenans may, in part, be distinguished by the degree and position of sulfation. Most sugar units have one or two sulfate groups esterified to a hydroxyl group at carbons C-2 or C-6. Suitable carrageenans include kappa carrageenan, iota carrageenan, and kappa II carrageenan and blends thereof. Sodium carrageenans are soluble at room temperature. Carrageenans can be prepared with low contents of gel-forming ions by known techniques. Carrageenan gels are thermoreversible. Higher levels of gel-forming ions may increase the temperature at which the gel can melted. Kappa carrageenans produce strong rigid gels while iota carrageenans are elastic and compliant. Kappa II carrageenans which are copolymers of kappa and iota form weak gels. Gel-forming ions for specific carrageenans are known in the art and include potassium and calcium. Lambda carrageenans do not form gels in water but may be useful in blends, for example, to modify the mechanical properties of the resulting gel. A preferred carrageenan is iota carrageenan. Iota carrageenan has a repeating unit of D-galactose-4-sulfate-3,6-anhydro-D-galactose-2-sulfate providing a sulfate ester content of about 25 to 34%.

A further preferred biopolymer comprises hyaluronic acid (HA), salts thereof and modified hyaluronate. Sodium hyaluronate is an abundant glycosaminoglycan found in the extracellular matrix of skin, joints, eyes and most organs and tissues of all higher animals. Non animal derived HA may be fermented from *Streptococcus zooepidemicus* Hyaluronic acid from a non-nimal source is preferred for use in the present invention. Hyaluronic acid is a linear copolymer composed of (β-1,4)-linked D-glucuronate (D) and (β-1,3)—N-acetyl-D-glucosamine (N). The coiled structure of hyaluronate can trap approximately 1000 times its weight in water. These characteristics give the molecule advantageous physicochemical properties as well as distinct biological functions and is desirable for use as a building block for biocompatible and biointeractive materials in pharmaceutical delivery, tissue engineering and viscosupplementation.

Hyaluronic acid or hyaluronate is a natural component in mammalian organisms and is enzymatically biodegradable by hyaluronidases. The half-life of hyaluronate in endothelial tissue is less than a day, and the natural turnover of the polymer in adults is approximately 7 g a day. A mild to moderate covalent modification of hyaluronan will increase the in vivo stability and retention time from days up to months or a year.

Suitable modified hyaluronates include those containing moieties covalently linked to the hyaluronates and may include for example peptide coupled hyaluronates. A preferred modified hyaluronate suitably has a covalently modified carboxyl group and/or hydroxyl group on the D and N monomer units respectively. Modified hyaluronates can be tailored by selection of moieties and their concentration in the modified hyaluronates to add, modify or alter properties or functionalities of the hyaluronates such as crosslinking capability, solubility, rate of biodegradability of the ability to bind, for example, specific cells, drugs or peptides.

Hyaluronic acid is thought to play an important role in the early stages of connective tissue healing and scarless fetal wound healing and regulate cell mobility, adhesion, and proliferation and is especially useful in tissue engineering and tissue regeneration applications.

Modified polysaccharides, also known as polysaccharide derivatives, may be employed in applications of the present invention so long as they are reactive with gel-forming ions. For example, alginate may be reacted with an alkylene oxide, such as ethylene oxide or propylene oxide, to form a glycol alginate. The glycol is bonded to the alginate through the carboxyl groups. Typically, alginate is reacted with propylene oxide to form propylene glycol alginate (PGA). Preparation of propylene glycol alginate is disclosed in Strong, U.S. Pat. No. 3,948,881, Pettitt, U.S. Pat. No. 3,772,266, and Steiner, U.S. Pat. No. 2,426,125. Preferably, the propylene glycol alginate has a degree of esterification of about 40% to about 95%, more preferably about 70% to 95%. Mixtures of propylene glycol alginates of different molecular weights may also be used. Aluminum ions are suitable for gelling glycol alginates.

Preferably, the foam is suitably prepared using a mixer, for example a kitchen aid mixer equipped with a wire whisk to aerate an aqueous solution of the polymer for producing the foam together with other components such as plasticizers for example, glycerin and sorbitol.

A foaming agent may be included in the aqueous dispersion to aid in foaming. When present, the foaming agent suitably produces a wet foam resistant to foam collapse. The foaming agent may be a single material or a mixture of materials that aid in foaming. The foaming agent may be a polymeric foaming agent, a surfactant, or a mixture thereof.

Polymeric foaming agents, such as surface active hydrocolloids, are generally preferred for most biological applications because they are harder to leach from the resulting gelled foam than surfactants. Examples of surface active hydrocolloids include methyl cellulose, hydroxy propyl methyl cellulose (HPMC), hydroxy propyl cellulose (HPC), hydroxy ethyl cellulose (HEC), albumin and glycol alginates, such as propylene glycol alginate. For some applications, it may be advantageous to add an additional polysaccharide, for example a cellulose derivative such as carboxymethyl cellulose, in addition to the foaming agent. The polymeric foaming agent is preferably soluble in water so that a homogeneous gelled foam is produced. Preferred water soluble foaming agents include albumin and hydroxy propyl methyl cellulose as they produce small bubbles that result in fine pores in the foam.

When dried cross-linked foams containing high levels of calcium are soaked in water, the foam structure typically does not break down due to the high level of crosslinking of the foam. However, the soluble components in the foam, including water soluble foaming agents such as hydroxy propyl methyl cellulose, may diffuse out of the foam. This loss of foaming agent may be prevented in, for example a wound healing application, by use a foaming agent that is not soluble under conditions of use. Some foaming agents form gels at body temperature, for example methyl cellulose forms gels above 35° C. When using a foam that comprises methyl cellulose as the foaming agent in an application in which the foam is at body temperature, the methyl cellulose will stay in the gelled state and remain in the foam and contribute to the wet strength of the foam.

When a polymeric foaming agent such as hydroxy propyl methyl cellulose is used, the concentration of the polymeric foaming agent in the aqueous dispersion is typically about 0.5 wt % to about 6 wt %, preferably about 1 wt % to about 4 wt %, more preferably about 1.5% to about 2 wt %. This produces a foam that comprises about 3 wt % to about 37 wt %, preferably about 6 wt % to about 25 wt %, more preferably about 6% to about 12.5 wt %, of the polymeric foaming agent, exclusive of water and any additive or additives that may be present in the foam.

For certain applications, a surfactant, with or without an added polymeric foaming agent, may be used as the foaming agent. Surfactants are well known to those skilled in the art and are described, for example, in *McCutcheon's Detergents and Emulsifiers*, and Laughlin, U.S. Pat. No. 3,929,678, incorporated herein by reference. Nonionic surfactants are typically condensation products of a hydrophobic organic aliphatic or alkyl aromatic compound and hydrophilic ethylene oxide and/or propylene oxide. The length of the resulting polyether chain can be adjusted to achieve the desired balance between the hydrophobic and hydrophilic properties. Nonionic surfactants include, for example, ethoxylates of alkyl phenols containing from about 8 to 18 carbon atoms in a straight- or branched-chain alkyl group, such as t-octyl phenol and t-nonyl phenol with about 5 to 30 moles of ethylene oxide, for example nonyl phenol condensed with about 9.5 moles of ethylene oxide, dinonyl phenol condensed with about 12 moles of ethylene oxide; ethoxylated and propoxylated alcohols, especially $C_{10\text{-}20}$ alcohols, with 2 to 100 moles of ethylene oxide and/or propylene oxide per mole of alcohol, especially ethoxylates of primary alcohols containing about 8 to 18 carbon atoms in a straight or branched chain configuration with about 5 to 30 moles of ethylene oxide, for example, the ethoxylates of decyl alcohol, cetyl alcohol, lauryl alcohol, or myristyl alcohol; ethoxylates of secondary aliphatic alcohols containing 8 to 18 carbon atoms in a straight or branched chain configuration with 5 to 30 moles of ethylene oxide; condensation of aliphatic alcohols containing about 8 to abut 20 carbon atoms with ethylene oxide and propylene oxide; polyethylene glycol and polyethylene oxide; ethoxylated castor oil (CREMOPHOR® CO 40); ethoxylated hydrogenated castor oil; ethoxylated coconut oil; ethoxylated lanolin; ethoxylated tall oil; ethoxylated tallow alcohol; and ethoxylates of sorbitan esters such as polyoxyethylene sorbitan monolaurate (TWEEN® 20), polyoxyethylene sorbitan monopalmitate (TWEEN® 40), polyoxyethylene sorbitan monostearate (TWEEN® 60), polyoxyethylene sorbitan monooleate (TWEEN® 80), and polyoxyethylene sorbitan trioleate (TWEEN® 85). For physical applications such as wound dressings, when a surfactant is included in the dried gelled foam, non-ionic surfactants, such as the ethoxylates of sorbitan esters, are preferred. Examples of anionic surfactants are sodium stearate, sodium cetyl sulfate, sodium lauryl sulfate, ammonium lauryl sulfate, triethanolamine lauryl sulfate, sodium myristyl sulfate, and sodium stearyl sulfate, triethanol amine dodecylbenzenesulfonate, sodium dodecylbenzene sulfonate, sodium polyoxyethylene lauryl ether sulfate, and ammonium polyoxyethylene lauryl ether sulfate. A preferred anionic surfactant is sodium lauryl sulfate (sodium dodecyl sulfate). Cationic surfactants include, for example, quaternary ammonium salts, such as cetyl trimethylammonium bromide, lauryl trimethyl ammonium chloride, alkyl benzyl methyl ammonium chlorides, alkyl benzyl dimethyl ammonium bromides, cetyl pyridinium bromide, and halide salts of quaternized polyoxyethylalkylamines. Zwitterionic surfactants can also be used.

When the surfactant is used with a polymeric foaming agent, a useful surfactant is a sorbitan ester, such as TWEEN® 20 surfactant. When a surfactant, such as TWEEN® 20 surfactant, is used with a polymeric foaming agent, the dried gelled foam may comprise about 0.05 wt % to 1.0 wt %, typically 0.1 wt % to 0.5 wt %, of the surfactant. However, for certain applications, such as oral care applications in which a surfactant, such as, for example, sodium lauryl sulfate, is used without a polymeric foaming agent, the dried gelled foam may comprise about 0.5 wt % to 5.0 wt %, typically 1.5 wt % to 3.0 wt %, of the surfactant, excusive of water and any additive or additives, such as silica or other abrasives or polishing agents, that may be present in the foam.

The components of a composite according to the invention for treatment of the human or animal body are desirably biocompatible and optionally biodegradable.

The foam itself may be used as a product in the same applications as the composite of the invention.

Suitable gel-forming ions for use in the present invention include monovalent and polyvalent ions, preferably a divalent and/or a trivalent ions, or mixture of ions capable of forming a gel with the polysaccharide or which do not form a soluble salt with the polysaccharide. Gel-forming ions for specific polysaccharides are known from the literature. For alginates, suitable polyvalent cations include, for example, calcium (2+), barium(2+), strontium(2+), iron(2+), zinc(2+), copper (2+), and aluminum(3+). Preferred cations are divalent metal cations, more preferably the calcium (2+) cation. A monovalent cation such as potassium would not be considered a gelling ion for an alginate since potassium alginate is a soluble alginate salt; however, the potassium cation would be a suitable gelling ion for kappa carrageenan or kappa 11 carrageenan. Where the polysaccharide salt is positively charged, for example, chitosan, negatively charged gel-forming ions, for example phosphate may be employed.

A salt or combination of salts that provides the desired gel-forming ions or mixture of gel-forming ions may be used as the gel-forming ions. Gel-forming ions may be incorporated in the foam either during preparation or subsequently added to the foam prior to addition of the liquid with the polysaccharide. Typical washing solutions for the polysaccharide foam have about 30 mM to about 200 mM, more preferably from 50 to 100 mM, of a water-soluble gelling salt such as calcium chloride, barium chloride, or strontium chloride. Suitably, the rate of gelation may be controlled to delay gelling by using sparingly soluble salts under pH conditions which they are slowly solubilized, or by using soluble gel-forming ions in combination with sequestrants. Washing or soaking can be used to modify the properties of the composite where additional gel-forming ions may be added to strengthen or harden the composite and also to control cell proliferation, while other treatments such as sequestrants or non-gel-forming ions may be used to weaken or dissolve the composite. Alginate gels can be dissolved by addition of an aqueous solution of citrate, EDTA or hexametaphosphate. Wash treatments for use with living cells must be isotonic. The properties of the composite may accordingly be tailored as desired.

The gel-forming ions may be able to form a gel with the polymer of the foam and/or the soluble polysaccharide. The gel-forming ions may form links between the foam and the soluble polysaccharide. Preferably, the "gel-forming ions" in the foam are donatable to the polysaccharide and are present in the foam at a level such that at least some of the gelling sites of the polysaccharide are occupied upon contacting the liquid component to the foam. Suitably, the gel-forming ions may be present in the foam at a sub-stoichiometric, stoichiometric or super-stoichiometric level with respect to sites in the foam for binding the gel-forming ions provided that sufficient gel-forming ions are present to occupy at least some of the gelling sites in the polysaccharide to be added.

In one embodiment, the gel-forming ions are not able to form a gel with the polymer of the foam.

In another aspect, the foam may comprise an excess of gel-forming ions relative to the gelling sites in the soluble polysaccharide. At least some of the gel-forming ions may be incorporated into the foam prior to addition of a soluble polysaccharide which then gels by interaction with the gel-forming ions within the foam structure.

The concentration of gel-forming ions may be controlled so that the resulting gel contains polysaccharide with gelling sites that are not fully reacted with gel-forming ions; i.e., the gel-forming ions or mixture of gel-forming ions is present in a molar amount less than that required to saturate 100% of the gelling sites of the polysaccharide. For example, when sufficient gel-forming ions, such as calcium ion, are present to react with all available gelling sites (eg. the L-guluronic acid units in the case of alginate, D-galacturonic acid units in the case of pectin substances), the gel-forming polymer is 100% saturated. The amount of cation required to completely saturate the gelling sites of alginate, for example, is considered to be 1 mole of divalent cation per 2 moles of L-guluronic acid in the alginate or 1 mole of trivalent cation per 3 moles of L-guluronic acid in the alginate when only a divalent cation or only a trivalent cation is used in the gelling. When a mixture of a divalent cation or cations and a trivalent cation or cations is used, the amounts required to saturate the alginate can be determined because a divalent cation occupies two gelling sites and a trivalent cation occupies three gelling sites. Thus, any amount less than this is considered to be an amount less than that required to completely saturate the gelling sites of the alginate. Suitably, the gel-forming ions present in the foam are sufficient to saturate about 5% to 250%, more suitably 5% to 200%, preferably about 35% to 150%, even more preferably about 50% to 100%, of the gelling sites of the polysaccharide.

The foam itself may be prepared using a polysaccharide and also requires gel-forming ions. In the case where both the foam and the polysaccharide rely on the same gel-forming ions, the foam alone may have an initial saturation when prepared, for example, of 150%, however when additional polysaccharide is added as a liquid and absorbed into the pores of the foam, some of the gel-forming ions are used to gel the added polysaccharide. In this case, the saturation of the added polysaccharide is calculated based on the total amount of gel-forming ions and the total amount of gelling sites for both the polysaccharide in the foam and the added polysaccharide forming the gels in the pores.

For alginate, the strength of gels formed by reaction of alginate with polyvalent cations is related to the molecular weight of the alginate, the guluronic acid content ("G content") of the alginate as well as the arrangement of guluronic and mannuronic acids on the polymer chain. In addition, the pore size, and thickness of the foam, the alginate concentration, the level of the gel-forming ions and the type of ions employed also contribute to strength. The G content of the alginate is suitably at least about 30%, preferably about 40% to about 90%, and more preferably about 50% to about 80%. Alginate derived from, for example, *Lessonia trabeculata* and from the stems of *Laminaria hyperborea* have a high G content and may, as a preference, be used to form the gelled foams of the invention. Fully saturated alginates with a high G content give gels with the highest mechanical strength.

The amount of divalent cation, such as calcium, required to react stoichiometrically with these G-blocks can be calculated for each alginate type by considering that two guluronic acid units plus one divalent cation are required to create one ionic crosslink. The amount of calcium required for stoichiometric saturation of a 1% sodium alginate solution are given in the following table:

| Seaweed Source | % G | mM Ca |
| --- | --- | --- |
| *Laminaria hyperborea* (stem) | 70 | 14-16 |
| *Laminaria hyperborea* (leaf) | 54 | 11-13 |
| *Lessonia trabeculata* | 68 | 13-15 |
| *Macrocystis pyrifera* | 39 | 8-9 |

A list of various commercially available alginates, their properties, and their sources is found in Shapiro, U.S. Pat. No. 6,334,968, Table 1, column 16, line 49, to column 17, line 18, incorporated herein by reference. Mixtures or blends of alginates, for example alginates of different molecular weights and/or G content, may be used as the gel-forming polymer.

Complete saturation (100% saturation) of the gelling sites occurs when the composition contains 1 mole of divalent cation per 2 moles of L-guluronic acid units. For example, an about 15 mM solution of calcium ion is required to 100% saturate a 1% solution of sodium alginate extracted from the stems of *Laminaria hyperborea*, an about 12 mM calcium solution is required to 100% saturate a 1% solution of sodium alginate extracted from the leaves (fronds) of *Laminaria hyperborea*, and an about 14 mM solution of calcium ions is required to 100% saturate a 1% solution of sodium alginate extracted from *Lessonia trabeculata*. Thus, when alginate is used as the gel-forming polymer, the gel-forming composition preferably comprises 0.2 to 0.9 mM of divalent cation, preferably 20% to 90% calcium (2+) ion, per 2 mM of L-guluronic acid units present in the alginate. When using a sparingly soluble salt as the gel-forming ions, the extent of cross-linking can be controlled by controlling either the amount of gelling agent, for example, calcium carbonate, and/or the amount of solubilizing agent, for example a pH modifier such as glucono delta-lactone, present during gel formation. Preferably, there should be a stoichiometric relationship between the pH modifier and the gelling agent such that substantially all gel-forming ions are available.

When all the gelling sites on the polysaccharide are not saturated with gel-forming ions, the remaining sites are occupied by non-cross-linking ions. If desired, active ions, such as the Ag(1+) cation, may be used to occupy some or all of the remaining sites. Scherr, U.S. 2003/0021832 A1, discloses that silver alginate may be used for the treatment of burns, wounds, ulcerated lesions, and related pathological states.

The liquid component suitable to add to the foam contains the polysaccharide dissolved in a solvent, typically water.

Examples of suitable soluble polysaccharides for producing the gel from the soluble polysaccharide include alginates, pectins, carrageenans, hyaluronates, chitosan and mixtures thereof. Alginates, chitosan and hyaluronates are preferred soluble polysaccharides.

The absorption rate of the liquid component and the rate of gelling of the polysaccharide may impact the structure of the composite. Absorption rate and absorptive capacity of the liquid component will depend upon foam characteristics such as pore size and volume, polysaccharide characteristics such as composition, and molecular weight; and liquid component properties relative to absorption such as solids concentration, and viscosity. When the viscosity of the liquid component impacts its ability to be rapidly absorbed into the foam, it may be suitable to use a lower concentration of the alginate or to use an alginate of a lower molecular weight.

Factors which affect the mechanical strength of the gel include the concentration of the polysaccharide, molecular weight of the polysaccharide, the chemical composition, the blend of different polysaccharide components as appropriate, for example the ratio of M-rich and G-rich alginates, the type and level of gel-forming ions and other components of the gel. The strength of the gel may be tailored by manipulating these parameters according to the intended application.

Suitably the viscosity of the liquid component is from about 5 mPas to about 1000 mPas, more typically about 8 mPas to 600 mPas, more preferably about 10 mPas to 200 mPas. The liquid component is preferably fully absorbed into the pores of the foam unless it is desired to create a gel layer on only a part of the foam, for example on the surface of the foam. The liquid should be sufficiently gelled so it is retained in the pores to avoid un-gelled or partially gelled material from leaking out of the foam unless it is desired to only coat the pores.

Gel formation will depend upon amount and type of gel-forming ions, polysaccharide characteristics such as composition and molecular weight; and liquid component properties relative to absorption such as solids concentration, and viscosity, and the relative proportion of liquid to the available pore volume. In some embodiments, the liquid will be absorbed, the polysaccharide begins to gel, and the gel will fill the pores. Other embodiments, for example, a substantial portion of the polysaccharide may gel as a coating on the pore walls as the liquid is absorbed.

A preferred polysaccharide is alginate. When alginate is used, the liquid typically comprises about 0.5 wt % to about 10 wt %, preferably about 1 wt % to about 6 wt %. A suitable weight-average molecular weight is about 4,000 Daltons to 500 000 Daltons, preferably 4000 to 300 000 Daltons. As used throughout, the weight-average molecular weight is determined using Size Exclusion Chromatography with Multiple Angle Laser Light Scatter Detection (SEC-MALS).

The liquid containing the polysaccharide may further include a functional component which is suitably disposed in, for example entrapped in the polysaccharide gel. Any functional component may be added so long as it does not prevent the liquid component from being absorbed into the foam or the polysaccharide from forming a gel. The functional component may be a liquid or a solid and, if insoluble, is dispersed as fine particles in the liquid. Desirable components to be disposed in the gel include beneficial agents such as flavors, fragrances, pharmaceutical and veterinary medicaments, enzymes, growth modifiers, and probiotics, living cells, including plant cells, animal cells, and human cells, yeasts, bacteria, and the like. Incorporation of pharmaceuticals, particulates, cells, multicellular aggregates, tissue, and the like may require gentle mixing in the polysaccharide, preferably alginate, solution. The component can include heat sensitive materials such as cells, drugs, flavors, or fragrances that may, if desired, later be released from the gel.

Where present, the functional component is selected according to the intended use of the composite. The composite suitably acts as a carrier for the functional component, releasing the component in use. The composite may be tailored to release the component in a particular manner particularly where the functional component is a pharmaceutical. The "release profile" of the component may be immediate, fast release, controlled release or pulsatile release as desired.

In some embodiments it is desired to release the entrapped component from the gel. Release may be achieved by physical attrition of the gel, extraction from the gel, or dissolution of the gel, or by simple diffusion or leakage from the gel. The process selected to release the component depends upon the application and the nature of the component to be released and could include application of mechanical or some energy, temperature or pH change, or addition of "de-gelling" agents such as chelating agents.

Composites of the present invention are useful in biomedical applications such as cell culture matrices, tissue engineering scaffold implants, and controlled release delivery systems for drugs, biologics, antibiotics and probiotic agents, and for food applications, industrial applications, and personal care applications such as cosmetic and oral hygiene.

In one embodiment, the invention provides a method to prepare sterile composites having cells, pharmaceuticals or particulates immobilized in gels within a sterile, dried alginate foam in one or two easy steps.

Applications for the sterile alginate composites include cell immobilization and/or cell proliferation for in vitro or in vivo tissue culture applications, cell therapy and artificial organs, a delivery system used in vivo for controlled release, for wound management, or as an anti-adhesion layer in vivo.

Devices for implantation in humans suitably have an endotoxin content of less than 350 EU per device. Ultrapure polysaccharides possessing a low content of endotoxins for example less than 350 EU/g, preferably less than 100 EU/g may be used, either for the foam or as the soluble polysaccharide, or both, as appropriate, depending upon what structure is intended for implantation into living animals and humans. For example, when alginates are used for implantation within the human body, the alginates suitably have an endotoxin content of less than 100 EU/g.

In a preferred embodiment the composite has an endotoxin content of less than 10 EU/g Composites of the present invention are useful in tissue growth and tissue engineering in which functional tissue is created using cells seeded on three dimensional scaffolds that provide a template to guide the growth of new tissue and ensure nutrients reach the cells and waste products are removed. The composite of the present invention can be engineered to facilitate the desired ingrowth and undergo degradation in a controllable and predictable manner. For example, when newly developed tissues propagate through the composite, the composite suitably degrades and provides space for new tissue formation. Composites can also be made which stimulate specific interactions with immobilized cells and/or cells in the area where the composite is implanted for example, by releasing cell-interacting molecules and growth factors for example for regeneration of bone, nerves, skin and cartilage. The composite can release growth factors to encourage ingrowth of cells based on a desired geometry and the controlled degradation of the implant allows the regenerated bone tissue to become load bearing. The composite of the present invention can be designed to promote or inhibit cell proliferation as appropriate by using calcium ions or strontium ions as the gel-forming ions, respectively.

Cells immobilized in the composite may be implanted into animals wherein the gel acts as an immune barrier and prevents detection by the immune system thereby allowing the implantation of xenografts. Suitably strontium can be used as gel-forming ions when animal cells are desired for implantation (xenografts), since when using this type of artificial organ, it is important that the cells do not grow out of the implanted composite and become exposed to the immune system. The composite may also be used to establish cell, tumor and tissue xenografts in animals for, for example, cancer research. Immobilization of multicellular aggregates, such as islets Langerhans, in the composite allows said multicellular aggregates to be implanted into animals or humans without immune rejection and such implanted cell aggregates may then function as an artificial organ producing, for example, insulin.

Cell cultures can be used to manufacture many biological materials, for example enzymes, hormones, immunobiologicals (such as monoclonal antibodies, interleukins, lymphokines) and anticancer agents. Cells can be cultured in composites according to the invention to increase the total number of cells. For example, cells isolated from a patient can be cultured in a composite of the invention to increase the cell number, the cells can then be retrieved from the composite and used in tissue engineering applications. Cell cultures in a composite according to the invention can also be used to explore, characterize and specify cell differentiation and growth to produce tissue like structures. For example, cells are affected by the external stress and modifying the elasticity of the composite (gel/foam) materials may influence gene expression.

Cells produced in vitro in the composite may suitably be recovered from the culture using a recovery agent. Suitable recovery agents include sodium citrate or other soluble salt of citric acid, sodium EDTA or other soluble salt of EDTA, and hexametaphosphate.

Without wishing to be bound by any theory, it is believed that the rigidity of the composite and the gel in which cells are immobilized are important factors for cell growth since it appears that the mechanical properties of the gel regulates proliferation, and differentiation has been observed based on cell type. The rigidity of the gel (as measured, for example, by elastic modulus) on which the cell is attached determines the magnitude of the force generated from the exoskeleton and the extent of cell spreading that ensues. The properties of alginate gels are varied by alginate concentration, saturation of gel-forming ions, and type of gel-forming ions. In addition, alginates can be chemically modified to add peptide sequences for cell adhesion, such as cell adhesion peptide sequences such as the RGD tripeptide.

Composites according to the invention may be used in the treatment of the human or animal body to prevent adhesion between tissue. Surgical interventions may cause conglutination or growing together of tissues, e.g. between muscles, between muscles and tendons or nerves or other tissues. To prevent this undesired tissue growth, an anti-adhesion layer can be inserted between muscles, muscles and tendons or nerves to cover the wound and prevent postoperative adhesion formation during the healing process. Composites of the present invention can be formulated for use as an anti-adhesion layer by selection of materials for example a hyalouronate foam in the composite and gelling ions which retards or prevents cell growth and intrusion into the anti-adhesion layer thus avoiding adhesion between tissues during healing. The composites can be engineered from biodegradable materials which dissolve as the wound heals (by appropriately varying the amount of cross linking ions, type of polymer, polymer concentration) and are degraded or excreted from the body.

Depending upon the formulation properties, the composite can be formulated to degrade over various periods of time and thereby release immobilized materials such as therapeutic agents or tissue-regenerative agents. A preferred use of the invention is in tissue repair wherein organic or inorganic material can be immobilized within the composite and act as a scaffold for tissue regeneration. One such example would be the inclusion of hydroxyapatite in the gel within the foam and then implanted into a bone defect in order to induce bone regeneration into the foam/gel composite. Another such example would be the inclusion of chemotactic or cell attractant substances within the composite followed by implantation of the composite in a tissue injury site in order to promote tissue regeneration.

When composites are to be used as controlled delivery applications, e.g. of pharmaceuticals, growth factors, nutriceuticals, flavors or fragrances, the mechanical and chemical properties can be modified for appropriate release in the desired environment.

| | Glossary |
|---|---|
| Albumin | Bovine albumin, Fraction V, approx. 99% (A-3059) (Sigma-Aldrich Chemie GmbH, Steinheim, Germany) |
| Antibiotic-Antimycotic | Antibiotic-Antimycotic solution (0710) GIBCO ® (Invitrogen Corp., Grand Island, NY, USA) |
| $C_2C_{12}$ | Mouse myoblast cell line (ATCC # CRL-1772) |
| $CaCl_2$ | Calcium chloride dihydrate, Ph. Eur. (Riedel-de Haën, Seelze, Germany) |
| $CaCl_2$ | Calcium chloride dihydrate (1.02382.1000) (Merck KgaA, Darmstadt, Germany) |
| $CaCO_3$ | Eskal 500, Calcium carbonate, particle size ~5.2 μm (KSL Staubtechnik, Launingen, Germany) |
| $CaCO_3$ | HuberCAL 500 Elite, Calcium carbonate, particle size ~4.2 μm (Huber Engineered Materials, Hamina, Finland) |
| $CaCO_3$ | HuberCAL 250 Elite, Calcium carbonate, particle size ~8.7 μm (Huber Engineered Materials, Hamina, Finland) |
| Calcein | Calcein, AM, 1 mg/ml (C3099) (Invitrogen, Molecular Probes, Eugene, Oregon, USA) |
| Citrate | Sodium citrate dihydrate, A.C.S Reagent (Sigma-Aldrich Chemie GmbH, Steinheim, Germay) |
| FBS | Fetal Bovine Serum, GIBCO ™ (Sigma-Aldrich Chemie GmbH, Taufkirchen, Germany) |
| Fluorescent dextran 10 kDa | Dextran, fluorescein, 10 000 Mw, anionic (D-1821) (Molecular Probes, Oregon, USA) |
| Fluorescent dextran 70 kDa | Dextran, fluorescein, 70 000 Mw, anionic (D-1822) (Molecular Probes, Oregon, USA) |
| GDL | Glucono δ-lactone (Roquette, Alessandria, Italy) |
| Glycerine | Glycerin, Ph. Eur. (VWR Prolabo, Leuven, Belgium) |
| Growth medium Chondrocytes | Dulbeccos's Eagle medium, modified (D-MEM) for Chondrocytes (61965-026) GIBCO ™ (Sigma-Aldrich Chemie GmbH, Taufkirchen, Germany). Added 10% heat inactivated FBS (20 minutes at 56° C.), 1% Antibiotic-Antimycotic and 1% sodium pyruvate. |
| Growth medium $C_2C_{12}$ cells | Dulbeccos's eagle medium, modified (D-MEM) for $C_2C_{12}$ cells (D-7777) (Sigma Chemical Co, St. Louis, MO, USA). Added 10% heat inactivated FBS (20 minutes at 56° C.), 3.7 g/l $NaHCO_3$, 10 ml/l non-essential aminoacids, 10 ml/l Penicillin-Streptomycin solution, 1.4 mg/l puromycin and MQ-water. |
| Growth medium MDCK cells | Minimum essential medium eagle (MEM) for MDCK cells (M0643) (Sigma Chemical Co, St. Louis, MO, USA). Added 10% heat inactivated FBS (20 minutes at 56° C.), 10 ml/l Penicillin-Streptomycin solution, 2.2 g/l $NaHCO_3$ and MQ-water. |
| GDL | Glucono δ-lactone (Roquette, Alessandria, Italy) |
| Glycerine | Glycerin, Ph. Eur. (VWR Prolabo, Leuven, Belgium) |
| Hanks' | Hanks' balanced salt solution; Modified; With $NaHCO_3$; Whithout phenol red, calcium chloride and magnesium chloride (Sigma-Aldrich Chemie GmbH, Steinheim, Germay) |
| HPMC | Pharmacoat 603, Substitution type 2910, Hypromellose USP, (hydroxypropylmethylcellulose) (Shin-Etsu Chemical Co. Ltd., Japan) |
| Isoton II | COULTER ® ISOTON ® II Diluent (Beckman Coulter, Krefeld, Germany) |
| Live/Dead test kit | Viability/Cytotoxicity kit for animal cells (Invitrogen, Molecular Probes, Eugene, Oregon, USA) |
| Mannitol | D-Mannitol 98% (Sigma-Aldrich Chemie GmbH, Steinheim, Germany) |
| MDCK | Madin Darby Canine Kidney cell line (ATCC #CCL-34) |
| MQ-water | MiliQ water |
| NaCl | Sodium chloride, p.a., (Merck, Darmstadt, Germany) |
| $NaHCO_3$ | Sodium bicarbonate (Sigma-Aldrich Chemie GmbH, Steinheim, Germany) |

| Glossary | |
|---|---|
| $Na_2HPO_4$ | Disodium hydrogen phosphate, art: 30427 (Riedel-de Häen, Seelze, Germany) |
| Na-triphosphate | Sodium triphosphate pentabasic (T5883-500G) (Sigma-Aldrich Chemie GmbH, Steinheim, Germany) |
| NOVATACH RGD | Peptide coupled PRONOVA UP MVG alginate, batch: CBIFMC01A02122005, sterile filtered and lyophilized. Peptide sequence: GRGDSP. Ratio peptide:alginate 9.11:1 |
| NOVATACH VAPG | Peptide coupled PRONOVA UP MVG alginate, batch: CBIFMC02A02122605, sterile filtered and lyophilized. Peptide sequence: VAPG. Ratio peptide:alginate 13.5:1 |
| Penicillin-Streptomycin | Penicillin-Streptomycin solution (P0781) (Sigma-Aldrich Chemie GmbH, Steinheim, Germany) |
| Protanal ® LF 200S | Sodium alginate, pharma grade, viscosity (1 wt % aqueous solution at 20° C.) = 302 mPas (FMC, Philadelphia, PA, USA) |
| PRONOVA UP MVG | Sodium alginate, batch: 701-256-11, viscosity (1 wt % aqueous solution at 20° C.) = 385 mPas (NovaMatrix, Oslo, Norway |
| PRONOVA UP LVG | Sodium alginate, batch: FP-502-04, viscosity (1 wt % aqueous solution at 20° C.) = 50 mPas (NovaMatrix, Oslo, Norway |
| PRONOVA SLG 100 | Sterile sodium alginate, viscosity (1 wt % aqueous solution at 20° C.) = 166 mPas (NovaMatrix, Oslo, Norway) |
| PRONOVA SLG 20 | Sterile sodium alginate, viscosity (1 wt % aqueous solution at 20° C.) = 37.5 mPas (NovaMatrix, Oslo, Norway) |
| PRONOVA SLM 20 | Sterile sodium alginate, viscosity (1 wt % aqueous solution at 20° C.) = 9.0 mPas (NovaMatrix, Oslo, Norway) |
| PRONOVA SLM 20 | Sterile sodium alginate, viscosity (1 wt % aqueous solution at 20° C.) = 92 mPas (NovaMatrix, Oslo, Norway) |
| PRONOVA UP LVG | Sodium alginate, viscosity (1 wt % aqueous solution at 20° C.) = 25 mPas (NovaMatrix, Oslo, Norway) |
| PRONOVA UP LVG | Ultrapure sodium alginate, batch: 221105, viscosity (1 wt % aqueous solution at 20° C.) = 35 mPas (NovaMatrix, Oslo, Norway) |
| PRONOVA UP LVG | Ultrapure sodium alginate, batch: FP-502-04, viscosity (1 wt % aqueous solution at 20° C.) = 50 mPas (NovaMatrix, Oslo, Norway) |
| PRONOVA UP LVG | Sodium alginate, viscosity (1 wt % aqueous solution at 20° C.) = 92 mPas (NovaMatrix, Oslo, Norway) |
| PRONOVA UP MVG | Ultrapure sodium alginate, batch: FP-310-01, viscosity (1 wt % aqueous solution at 20° C.) = 296 mPas (NovaMatrix, Oslo, Norway) |
| PRONOVA UP MVG | Ultrapure sodium alginate, batch: FP-312-03, viscosity (1 wt % aqueous solution at 20° C.) = 248 mPas (NovaMatrix, Oslo, Norway) |
| PRONOVA UP MVG | Ultrapure sodium alginate, batch: 701-256-11, viscosity (1 wt % aqueous solution at 20° C.) = 385 mPas (NovaMatrix, Oslo, Norway) |
| PROTASAN CL 210 (214) | Chitosan chloride, batch: 708-783-01, deacetylation: 94.5%, pH = 5.3, viscosity of 1% aqueous solution at 20° C. = 77 mPas (NovaMatrix, Oslo, Norway) |
| PROTASAN UP CL 213 | Ultrpure chitosan chloride, batch: FP-104-02, viscosity (1 wt % aqueous solution at 20° C.) = 74 mPas, degree of deacetylation = 86% (NovaMatrix, Oslo, Norway) |
| Propidium Iodide | (P4170) (Sigma Chemical Co., St. Louis, MO, USA) |
| Puromycin | Puromycin dihydrochloride (P7255) (Sigma Chemical Co., St. Louis, MO, USA) |
| Sodium Hyaluronate | Pharma grade 80, batch: 17053P, molecular weight: $1.08 * 10^6$ g/mole (NovaMatrix for Kibun Food Kemifa Co., Ltd., Kamogawa, Japan) |
| Sodium pyruvate | Sodium pyruvate 100 mM solution (S-8636) (Sigma Chemical Co., St. Louis, MO, USA) |
| Sorbitol, | D(−)sorbitol for biochemistry, dry, 100% (Merck, KGaA, Darmstadt Germany) |
| Sorbitol special | 70% sorbitol solution (SPI Polyols, New Castle, DE, USA) |
| $SrCl_2$ | Strontium chloride hexahydrate 99% A.C.S. Reagent (Sigma-Aldrich Chemie GmbH, Steinheim, Germay) |
| $SrCO_3$ | Strontium carbonate 99.9+% (Sigma-Aldrich Chemie GmbH, Steinheim, Germay) |

EXAMPLE 1

This example shows how the stiffness or the elasticity of the foams is varied as a function of saturation with gel-forming ions and temperature.

The wet foam formulations for the three different foams tested are presented in Table 1. The formulations vary the calcium carbonate such that the calcium ions are sufficient to saturate the gelling sites of the alginate with 66%, 111% and 155%, respectively.

TABLE 1

Wet foam formulations.

| Ingredient | 66% saturated | 111% saturated | 155% saturated |
|---|---|---|---|
| 4% alginate solution (PRONOVA UP MVG, 701-256-11) | 111.2 | 111.2 | 111.2 |
| Glycerin | 6.0 | 6.0 | 6.0 |
| Sorbitol special | 18.0 | 18.0 | 18.0 |
| HPMC | 3.0 | 3.0 | 3.0 |
| CaCO$_3$ (HuberCAL 500 Elite) | 0.45 | 0.75 | 1.03 |
| GDL | 1.61 | 2.69 | 3.77 |
| MQ-water | 59.7 | 58.4 | 57.0 |
| Total, Amount in [g] | 200.0 | 200.0 | 200.0 |

An aqueous solution of alginate was prepared and set aside. Calcium carbonate was dispersed in the water (25 grams less than amount shown in Table 1) in a mixing bowl. Glycerin, sorbitol special, the aqueous alginate solution, and HPMC were added to the same bowl and the dispersion was blended with a Hobart kitchen aid mixer equipped with a wire whisk at medium speed for one minute to ensure homogeneity. Mixing continued an additional seven minutes at high speed before adding a freshly mixed GDL solution (ie, the GDL plus the 25 grams of water) and further mixing at high speed for 1 minute, which gave a resulting wet foam density of 0.25 g/ml (as determined from the weight of wet foam required to fill a 100 ml container). The foams were cast in 2 mm high molds coated with Versi-Dry bench protector with the polyethylene side towards the foam (Nalgene Nunc International, NY, USA) and kept uncovered for 60 minutes at room temperature before drying at 80° C. in a drying oven for 30 minutes. The dried sheets of foams appeared somewhat different as they varied in pore size and thickness. As the gelling rate of the wet foam material is correlated with the saturation with gel-forming ions, coalescence of pores will occur most for the lowest saturated foams.

Circular patches with a diameter of 2.1 cm were stamped out of the dried foam sheets. Some of the foam patches from the 111% saturated foam were autoclaved at 121° C. for 20 minutes.

The foam was prepared for mechanical testing by placing a foam patch in a Petri dish with a diameter of 3.5 cm and adding 4 ml of a model physiological solution (2.5 mM CaCl$_2$ and 9 mg/ml NaCl). The foam was kept in this solution for 5 minutes before it was transferred to a Bohlin CVO 120 High Resolution Rheometer. The foam was placed between serrated plates (PP 25) with a gap of 500 µm prior to oscillation measurements. Stress sweeps were performed with an applied shear stress from 0.5 Pa to 50 Pa. The frequency was set to 1 Hz. The sweep was performed three times for each foam patch. The elastic modulus, G', read in the linear viscoelastic region ($G'_{lin}$) is reported in Table 2. Tests were performed at two different temperatures. The temperature of the added physiological solution, temperature during swelling, and during the measurements was either 20° C. or 37° C.

TABLE 2

$G'_{lin}$ of Foam Compositions at two temperatures (n = 3).

| Foam | $G'_{lin}$ ± SEM at 20° C., [Pa] | $G'_{lin}$ ± SEM at 37° C., [Pa] |
|---|---|---|
| 66% saturated | 762 ± 5 | 736 ± 29 |
| 111% saturated | 2375 ± 52 | 1820 ± 41 |
| 111% saturated (autoclaved) | 2469 ± 39 | Not tested |
| 155% saturated | 5374 ± 358* | 3943 ± 195 |

*n = 6

The data show an increase in elastic modulus as a function of increased amount of gel-forming ions. Autoclaving conditions did not seem to affect the foam modulus at 111% saturation.

EXAMPLE 2

This example shows how gel-forming ions diffuse from the foam to an added alginate solution and thereby induce gelling. The elastic modulus was measured as a function of time after the alginate solution was added to describe the gelling kinetics and the increase in material elasticity.

A composite was prepared from dry foam disks (2.1 cm in diameter) from the same 66% and 111% saturated foams prepared in example 1 and 250 µl 1% PRONOVA UP LVG (99 mPas) by uniformly distributing the solution by dropwise addition from a pipette onto the top surface of the foam. All of the alginate solution added was absorbed and it filled pores through the foam. The calcium ions present in the 66% and the 111% saturated foams saturate 43% and 71% of the total amount of alginate in the composite. The composite was transferred to the rheometer 5 minutes after addition of the alginate solution. The gap was set to 300 µm and the frequency and strain were kept constant at 1 Hz and 0.001 respectively. The elasticity modulus, G, of the composite as a function of time is presented in Table 3.

TABLE 3

G as a function of time after addition of alginate solution to the foams

| | G ± SEM at 20° C., [Pa] | |
|---|---|---|
| Time, [min] | 66% saturated foam | 111% saturated foam |
| 6 | 828 | 1787 |
| 15 | 858 | 2931 |
| 30 | 893 | 3499 |
| 45 | 919 | 3863 |
| 60 | 942 | 4020 |
| 75 | 970 | 4059 |
| 90 | 997 | 3986 |
| 105 | 1067 | 4027 |

The results show an increase in elastic modulus as a function of time for both foams, which indicate the diffusion of gel-forming ions from the alginate foam to the added alginate solution and the resulting gelling. The values of G increase fast and reach a plateau after 60 minutes for the 111% saturated foam. For the 66% saturated foam the G values are lower, increase more slowly and the results indicate that the diffusion was not completed within the 105 minutes with testing.

EXAMPLE 3

This example shows how the elasticity of the composite biomaterials can be modified with use of foams containing varying amounts gel-forming ions and by adding alginate solutions with different G-content and molecular weight.

The foams tested was the 111% saturated foam and the 111% saturated foam which had been autoclaved from example 1, and a new 155% saturated foam prepared as in example 1 except using a blend of calcium carbonate where half of the $CaCO_3$ was replaced with a $CaCO_3$ with larger particle diameter (HuberCAL 250 Elite, 8.7 µm). This foam had somewhat larger pores than the 155% saturated foam from example 1 and was able to absorb more alginate solution with a higher viscosity. The wet density of the 155% saturated foam was 0.24 g/ml. Foam disks (diameter 2.1 cm) as example 1 were placed in petri dishes and added on the top surface 250 µl alginate solution with use of a pipette. All of the alginate solution added was absorbed and it filled the pores through the foams. The dishes containing foams with alginate solution added were kept at room temperature for 60 minutes and then 4 ml of the model physiological solution was added. After 5 minutes, the disc was transferred to the rheometer and a stress sweep was performed as described in example 1 except the gap was set to 300 µm. The measured $G'_{lin}$ for these samples are presented in Table 4. The G-content of the PRONOVA UP LVG is about 67% (high-G) whereas PRONOVA SLM 20 contains about 43% G (high-M). The alginate samples with the lower viscosity were prepared by degradation of the molecular weight of the alginate by autoclaving 1% and 2% solutions of the PRONOVA SLM 20 and PRONOVA UP LVG, respectively, for 20 minutes at 121° C.

TABLE 4

$G'_{lin}$ of composites with varying alginate concentration of the added alginate solution for two molecular weights (1% viscosity) of high M alginate

| Foam saturation | PRONOVA SLM 20 alginate | Overall composite saturation | $G'_{lin}$ ± SEM at 20° C., [Pa] for composites with SLM 20 visc = 9 mPas | $G'_{lin}$ ± SEM at 20° C., [Pa] for composites with SLM 20 visc = 92 mPas |
|---|---|---|---|---|
| 111% | 1.0% | 82% | 3373 ± 24 | 4063 ± 208 |
| 111% | 0.75% | 88% | 2856 ± 139* | 3846 ± 196 |
| 111% | 0.5% | 94% | 2720 ± 164* | 3498 ± 168 |
| 111% | 0.25% | 102% | 2963 ± 38 | 3089 ± 231 |

(*n = 5)

TABLE 5

$G'_{lin}$ of composites with varying concentration of the added alginate solution for two molecular weights (1% viscosity) of high G alginate

| Foam saturation | PRONOVA UP LVG alginate | Overall composite saturation | $G'_{lin}$ ± SEM at 20° C., [Pa] for LVG visc = 25 mPas | $G'_{lin}$ ± SEM at 20° C., [Pa] For LVG visc = 99 mPas |
|---|---|---|---|---|
| 155% | 1.0% | 98% | 5037 ± 209 | not tested |
| 155% | 0.5% | 120% | 3792 ± 185 | not tested |
| 111% | 1.2% | 67% | 4344 ± 44 | 5060 ± 259* |
| 111% | 1.0% | 71% | 3870 ± 197 | 4740 ± 71 |
| 111% | 0.75% | 78% | 3485 ± 114 | 3522 ± 115 |
| 111% | 0.5% | 87% | 3189 ± 61 | 3147 ± 70 |
| 111% | 0.25% | 97% | 3241 ± 174 | 2786 ± 100 |
| 111% Autoclaved | 1.0% | 71% | not tested | 4768 ± 147 |

(*n = 5)

The data show that the composites with the highest elastic modulus at both 1.0% and 0.5% added alginate were 155% saturated foams with the added high-G alginate. The molecular weight of the alginate is of importance for both high-G and high-M alginates as the elastic modulus $G'_{lin}$ decreased with decreasing viscosities, except for alginate concentrations of 0.75% and below for the high-G alginate where similar results were obtained. In general, the elastic modulus $G'_{lin}$ decreased as the concentration of the alginate added decreased for both the 155% and the 111% saturated foams, and for the four different alginates. Exceptions were observed for the low viscosity alginates at lowest concentrations. The elastic modulus G in of the composite was not altered by autoclaving the foam.

EXAMPLE 4

This example shows how the elasticity of the composite material is influenced by washing the composite in a solution containing additional gel-forming ions.

Dry foam disks (diameter about 2.1 cm) from the 111% saturated foam in example 1 were placed in Petri dishes and 250 microliters 1% PRONOVA UP LVG (99 mPas) was added to the top surface of the foams and held at room temperature 60 minutes. Then the composites were incubated in 4 milliliters of either a 50 mM solution of $CaCl_2$ or a 50 mM solution of $SrCl_2$. After 5 minutes was the solution containing extra gel-forming ions was replaced with model physiological solution and after another 5 minutes was the $G'_{lin}$ measured as described in example 1. Another sample which did not receive any added extra gel-forming ions had the model physiological solution added 60 minutes after the alginate was added, and the $G'_{lin}$ was measured after 5 minutes swelling. The results are presented in Table 6.

TABLE 6

Modulus $G'_{lin}$ of composites prepared with and without washing in a solution containing extra gel-forming ions (n = 3).

| Wash | $G'_{lin}$ ± SEM at 20° C., [Pa] |
|---|---|
| 50 mM $CaCl_2$ | 13 100 ± 700 |
| 50 mM $SrCl_2$ | 15 900 ± 600 |
| Not washed | 2 700 ± 100 |

The data show more than four to nearly six times increase in elastic modulus $G'_{lin}$ by washing the composites with a solution containing calcium or strontium ions respectively. A higher value was obtained for the composites washed in the solution containing strontium ions which created a more rigid gel network than the composite washed with calcium ions.

EXAMPLE 5

This example shows how proliferation and viability of MDCK (Madin Darby Canine Kidney) cells immobilized in alginate are influenced by varying the calcium saturation of the alginate foam, and the effect of adding additional gel-forming ions to the composite after cell immobilization.

Two different alginate foams were prepared with calcium ions sufficient to saturate 100% and 200% of the gelling sites of the alginate. The wet foam formulations are presented in Table 7.

TABLE 7

Wet foam formulations.

| Ingredient | 100% Saturated foam | 200% Saturated foam |
|---|---|---|
| 4% alginate solution (PROTANAL LF 200 S) | 125 | 125 |
| Glycerin | 6.0 | 6.0 |
| Sorbitol special | 18.0 | 18.0 |
| HPMC | 3.0 | 3.0 |
| $CaCO_3$ (Eskal 500) | 0.76 | 1.52 |
| GDL | 2.66 | 5.32 |
| Deionized water | 44.6 | 41.2 |
| Total [amount in g] | 200.0 | 200.0 |

An aqueous solution of alginate was prepared. Then the $CaCO_3$ was dispersed in the water as listed above, except for 25 g, in a mixing bowl. Glycerin, sorbitol special, the aqueous alginate solution and HPMC were added to the same bowl and the dispersion was blended with a Hobart kitchen aid mixer equipped with a wire whisk at medium speed for 1 minute to ensure homogeneity. For the 100% saturated foam, mixing continued for 3 minutes at high speed. GDL was then dissolved in the remaining 25 g of water and added to the wet foam. The dispersion was further mixed at high speed for 30 seconds. The resulting wet density of the 100% foam was 0.23 g/ml. For the 200% saturated foam, the high speed mixing time was 3.5 minutes before GDL addition and then additionally 15 seconds of high speed mixing. The 200% foam had a wet density of 0.26 g/ml. Both foams were cast in 1 mm high Teflon coated molds and kept uncovered for 15 minutes at room temperature before drying at 80° C. in a drying oven for 30 minutes.

Disks (diameter=3.6 cm) were cut from the dried foam sheets with a scalpel and packed separately. The foam disks were then autoclaved at 121° C. for 20 minutes.

Sterile alginate (PRONOVA SLG 100) was dissolved in cell growth medium (MEM) to a 1% alginate solution. The alginate solution and a suspension of MDCK cells in growth medium were blended to a final concentration of 0.8% alginate and 200 000 cells/ml. The alginate foam discs were transferred to wells in a 6 wells plate (Nunclon®, Nalgene Nunc International), where they closely fit the well size. 1.0 ml of the alginate cell suspension was distributed drop-wise with a pipette to each of the foams and the alginate composites were incubated at 37° C. for 20 minutes. The calcium ions present in the 100% and 200% saturated foam were sufficient to saturate 67% and 133% of the gelling sites of the total amount of alginate, respectively. Half of the samples were then given a washing post treatment by adding them to about 5 ml of an aqueous solution containing 50 mM $CaCl_2$ and 104 mM NaCl. After 10 minutes, the salt solution was replaced with cell growth medium. To the remaining samples cell growth medium were added after the 20 minutes of incubation. The alginate composites with the immobilized cells were kept at 37° C. and growth medium were changed three times a week.

Quantification of cell proliferation and viability were measured after different times after immobilization. The immobilized cells were isolated by transferring the alginate composites to centrifuge tubes containing about 8 ml isotonic citrate solution (50 mM trisodiumcitrate dihydrate and 104 mM NaCl). The tubes were regularly gently turned until the composite was dissolved within about 2-10 minutes, and then centrifuged at 13 000 rpm for 5 minutes. The supernatants were poured off and the pellets containing the cells were re-suspended in 1.0 ml 250 mM mannitol. Three samples of each of 100 microliters, 80 microliters, and 50 microliters of the re-suspended pellets were then transferred to wells in a 96 wells plate (Nunclon®, Nalgene Nunc International). Then zero, 20 microliters, and 50 microliter of mannitol respectively were added (i.e., to fill each well to a total of 100 microliters) and then a further 100 microliters of live/dead reagent. The live/dead reagent was made from 5 ml mannitol solution (250 mM), 20 microliters ethidium solution (2 mM) and 5 µl calcein solution (4 mM). Standard curves were prepared from viable and ethanol fixed cells within the range of $0-10^6$ cells.

The cell proliferation and viability were measured with use of Cytofluor microplate reader. The filters used for Calcein were 485 nm (excitation) and 530 nm (emission), and for Ethidium were 530 nm (excitation) and 620 nm (emission).

TABLE 8

Cell viability and proliferation as a function of time from varying composites (n = 3, ± SEM).

| Sample type | Age | Total cell count | Normalized | Dead cells, % |
|---|---|---|---|---|
| 100% unwashed | 1 week | 231 800 ± 10,200 | 1.2 ± 0.1 | 9 ± 2 |
| | 3 week | 130 300 ± 28 700 | 0.65 ± 0.14 | 63 ± 18 |
| | 5 week | 224 700 ± 121 000 | 1.1 ± 0.6 | 45 ± 23 |
| | 7 week | 196 800 ± 28 400 | 1.0 ± 0.1 | 55 ± 9 |
| 100%, washed | 1 week | 189 600 ± 5 100 | 0.95 ± 0.03 | 7 ± 2 |
| | 3 week | 304 900 ± 31 500 | 1.5 ± 0.2 | 37 ± 4 |
| | 5 week | 322 200 ± 82 800 | 1.6 ± 0.4 | 39 ± 11 |
| | 7 week | 660 300 ± 394 600 | 3.3 ± 2.0 | 40 ± 8 |
| 200% unwashed | 1 week | 212 600 ± 34 700 | 1.1 ± 0.2 | 8 ± 3 |
| | 3 week | 258 300 ± 62 500 | 1.3 ± 0.3 | 43 ± 4 |
| | 5 week | 283 400 ± 73 300 | 1.4 ± 0.4 | 44 ± 6 |
| | 7 week | 364 800 ± 22 300 | 1.8 ± 0.1 | 60 ± 2 |
| 200%, washed | 1 week | 255 600 ± 48 900 | 1.3 ± 0.2 | 8 ± 2 |
| | 3 week | 712 800 ± 292 600 | 3.6 ± 1.5 | 18 ± 2 |
| | 5 week | 485 600 ± 217 400 | 2.4 ± 1.1 | 28 ± 5 |
| | 7 week | 663 600 ± 176 500 | 3.3 ± 0.9 | 42 ± 5 |

The data in Table 8 show that the washing step adding extra calcium ions (which provides a more rigid gel network) promotes cell proliferation. As the number of cells increased over time, decreased cell viability was observed.

Investigating the composites in a fluorescence microscope after soaking them in the live/dead reagent showed that the washed composites samples had more cells spreading out.

EXAMPLE 6

This example shows how proliferation and viability of fast growing myoblast cells from mouse ($C_2C_{12}$ cells) are affected by the washing step after cell immobilization and the effect of the type of gel-forming ions in the washing solutions.

An alginate foam was made with calcium as gel-forming ions, sufficient to saturate the alginate by 155%. The wet foam formulation is presented in Table 9.

TABLE 9

Wet foam Formulation.

| Ingredient | Amount, [g] |
|---|---|
| 4% alginate solution (PRONOVA UP MVG, FP-312-03) | 113.0 |
| Glycerin | 6.0 |
| Sorbitol special | 18.0 |
| HPMC | 3.0 |
| CaCO$_3$ (HuberCAL 500 Elite) | 1.05 |
| GDL | 3.77 |
| MQ-water | 57.0 |

The wet foam was prepared as described in Example 5, except high speed mixing for 7 minutes before the addition of GDL dissolved in 30 g of the total water followed by an additional 30 seconds high speed mixing. The resulting wet foam density was 0.29 g/ml and the foam was cast in a 2 mm deep mold coated with Versi-Dry bench protector with the polyethylene side towards the foam. The foam was then kept uncovered at ambient temperature for 1 hour before it was dried in a drying oven at 80° C. for 30 minutes.

Disks (diameter=2.1 cm) were stamped out from the dried foam sheets and packed separately. The foam disks were then autoclaved at 121° C. for 20 minutes.

The sterile alginate foams were transferred to wells in a 12 well plate (Nunclon®, Nalgene Nunc International), where they closely fit the well size. 300 µl of a 1% alginate solution (PRONOVA SLG 20) containing 25,000 cells were distributed drop-wise with a pipette to the foam. The foams were then incubated for 20 minutes at 37° C. The calcium ions present in the foam were sufficient to saturate the total amount of alginate in the composite by 97%. Growth medium (D-MEM) was added to one-third of the foams. About 2 milliliters of an isotonic calcium solution (50 mM CaCl$_2$ and 250 mM mannitol) was added to half of the remaining foams, while the other half of the remaining foams received an isotonic strontium solution (50 mM SrCl$_2$ and 250 mM mannitol). The gelling solutions were replaced with growth medium after about 2-5 minutes. The foams with the immobilized cells were kept at 37° C. and growth medium was changed three times a week.

Quantification of cell proliferation and viability were measured twice, at day 1 and at 10 weeks after immobilization (FIGURE 2). The immobilized cells were isolated as described in Example 5, except different de-gelling solutions were used for the day 1 and 10 week tests. The foams tested 1 day after cell immobilization were dissolved in 10 ml of a solution containing 50 mM citrate and 250 mM mannitol. The foams tested 10 weeks after cell immobilization were dissolved in 10 ml of Hanks' solution containing added 50 mM citrate. The recovered cell pellets were dispersed in 1 ml of Live/dead reagent (made from 4 ml Isoton II, 1 ml propidium iodide (85 µg/ml) and 20 µl calcein (1 mg/ml). Two drops were added a Bürker counting chamber for cell counting in a fluorescence microscope, while the rest of the cell dispersion were filtered through a 60 µm nylon mesh and then five minutes after resuspension, the cells were analyzed with use of a Coulter EPICS Elite flow cytometer.

TABLE 10

Proliferation and viability of C$_2$C$_{12}$ cells in three different composites presented as the mean of 3 or 4 composites ± SEM.

| | Cell proliferation, total number of cells | Cell proliferation, normalized, [%] | Dead Cells, [%] |
|---|---|---|---|
| Foam without wash | | | |
| 1 day | 19,900 ± 1,600 | 0.8 ± 0.1 | 28 ± 3 |
| 10 weeks | 216,300 ± 5,200 | 8.7 ± 0.2 | 70 ± 6 |
| Foam with CaCl$_2$ wash | | | |
| 1 day | 25,500 ± 1,600 | 1.0 ± 0.1 | 21 ± 4 |
| 10 weeks | 349,000 ± 66,400 | 14 ± 3 | 72 ± 4 |
| Foam with SrCl$_2$ wash | | | |
| 1 day | 14,400 ± 1,200 | 0.6 ± 0.1 | 32 ± 0 |
| 10 weeks | 117,000 ± 11,500 | 4.7 ± 0.5 | 72 ± 6 |

The results show an increase of the total cell number in all three composites. The proliferation of C$_2$C$_{12}$ cells is most highly promoted for cells immobilized in the composites that were washed with a solution containing additional calcium ions after cell immobilization. The slowest growing cells were those cells immobilized in the composites which were washed with a solution containing strontium ions after cell immobilization.

Investigating the composites in a fluorescence microscope showed that the cells immobilized in the composites washed with calcium ions were stretched out and grew both on and through the structure. The cells immobilized in the composites washed with strontium ions were visible as single cells or small clusters.

EXAMPLE 7

This example shows how cell proliferation and viability of human chondrocytes are affected by varying the source of gel-forming ions in the alginate foam, the washing step after cell immobilization and the effect of the different gel-forming ions in the washing solutions.

Alginate foams were made with either calcium or strontium as the gelling ion sufficient to saturate the alginate by 155% and 105% respectively. The wet foam formulations are presented in Table 11.

TABLE 11

Wet Foam Formulation.

| Ingredient | Ca-foam | Sr-foam |
|---|---|---|
| 4% alginate solution (PRONOVA UP MVG, FP-310-01) | 107.8 | 107.8 |
| Glycerin | 6.0 | 6.0 |
| Sorbitol special | 18.0 | 18.0 |
| HPMC | 3.0 | 3.0 |
| CaCO$_3$ (HuberCAL 500 Elite) | 1.05 | 0 |
| SrCO$_2$ | 0 | 1.05 |
| GDL | 3.77 | 3.77 |
| Deionized water | 57.0 | 57.0 |
| Total, Amount in [g] | 200.0 | 200.0 |

The wet foams were prepared as described in Example 6, except using 8 minutes with high speed mixing before addition of GDL dissolved in 30 g water of the total water and using 45 seconds of final high speed mixing. The resulting wet foam densities were 0.30 g/ml and the foams were cast in 2 mm deep molds coated with Versi-Dry bench protector. The foams were then kept uncovered at ambient temperature for 1 hour before they were dried in a drying oven at 80° C. for 30 minutes.

Sterile alginate foam disc preparation and addition of cells to the foams were done as described in Example 7 except that 300 µl of a 1% alginate solution (PRONOVA SLG 20) with 195,000 cells/ml was added to the foams. The gel-forming ions present were sufficient to saturate the total of G-monomers in the alginates by 97% and 63% for the foam gelled with calcium ions and the foam gelled with strontium ion respectively Quantification of cell proliferation and viability were measured twice, at 2 weeks and 11 weeks after immobilization of cells in the alginate foams gelled with Calcium ions (Ca-foams), and once after 13 weeks for the alginate foams gelled with Strontium ions (Sr-foams) and such data are shown in Table 12. The immobilized cells were isolated as described in Example 6, except 15 ml degelling solution (Hanks with 50 mM citrate) were used for the Sr-foams. The sample preparation for cell quantification and use of the flow cytometer were as described in Example 6.

TABLE 12

Proliferation and viability of Chondrocytes in six different composites presented as the mean of 3 or 4 composites ± SEM.

| Foam | Wash | Time | Total cell count | Normalized cell count | dead cells, % |
|---|---|---|---|---|---|
| Ca-foam | none | 2 weeks | 36,800 ± 3,000 | 0.6 ± 0.1 | 28 ± 4 |
| Ca-foam | none | 11 weeks | 65,400 ± 4,200 | 1.1 ± 0.1 | 50 ± 4 |
| Ca-foam | CaCl$_2$ | 2 weeks | 50,600 ± 1,800 | 0.9 ± 0.1 | 22 ± 2 |
| Ca-foam | CaCl$_2$ | 11 weeks | 132,700 ± 12,900 | 2.3 ± 0.4 | 64 ± 5 |
| Ca-foam | SrCl$_2$ | 2 weeks | 32 800 ± 2,500 | 0.6 ± 0.1 | 27 ± 2 |
| Ca-foam | SrCl$_2$ | 11 weeks | 35 400 ± 4,800 | 0.6 ± 0.2 | 36 ± 2 |
| Sr-foam | none | 13 weeks | 40,800 ± 2,100 | 0.7 ± 0.1 | 48 ± 2 |
| Sr-foam | CaCl$_2$ | 13 weeks | 89,700 ± 11,600 | 1.5 ± 0.1 | 63 ± 5 |
| Sr-foam | SrCl$_2$ | 13 weeks | 52,700 ± 1,800 | 0.9 ± 0.1 | 34 ± 3 |

The results described in Table 12 show that the alginate matrices in composites washed with calcium ion solution had at least twice as many cells after 11 weeks as the other composites. This indicates promoted cell proliferation due to additional calcium ion and/or its effect of providing a more rigid gel matrix. The results also show an inhibited cell proliferation for the cells immobilized in matrixes in composites washed in strontium ion solution. The similar trends were observed for the strontium foams. Strontium foams washed with calcium ion showed the most cell growth of the strontium foam series. The strontium foams without washing or washed with the strontium containing solution showed little or no increase in total cell number. Increased cell death was observed over time as the cells proliferated. Highest percentages of viable cells were observed in the composites containing the slowest growing cells. Investigating the composites in a fluorescence microscope showed that the cells immobilized in the calcium washed composites stretched out and grew both on and through the structure. The cells immobilized in the composites washed with strontium ions were visible as single cells or small clusters.

EXAMPLE 8

This example shows how composite biomaterials can be used as a matrix providing controlled release of an immobilized material and how the release profile can be modified as a function of the size of the immobilized material.

The alginate foams tested was the same as presented in Example 1 and had calcium incorporated sufficient to saturate 111% of the gelling sites of the alginate. Foam discs with a diameter of 1.0 cm were stamped out with a cork borer. An 1.1% aqueous alginate solution was made from PRONOVA UP LVG (FP-502-04). This alginate solution was diluted with MQ-water and a solution with fluorescent dextran (6.25 mg/ml) to give four different solutions varying in alginate concentration and type of fluorescent dextran as presented in Table 13. 80 µl of a solution containing alginate and fluorescent dextran was pipetted onto an alginate foam disc and after 10 minutes the solution was fully absorbed into the foam. The calcium present in the alginate foam was enough to saturate the gelling sites in the total amount alginate in the solution and the foam by 62%. The amount of fluorescent dextran added to each of the foam discs was 45.63 µg. The foam discs were kept in room temperature only covered with alumina foil to avoid light. Each of the foam discs was then separately transferred into a tube containing 10 ml Hanks'. The tubes were horizontally stirred at approx. 20 rpm and samples of 100 µl were collected for quantification of fluorescent dextran that might have leaked out of the composite. The concentration of fluorescent dextran in the collected samples and standard solutions (fluorescent dextran 10 kDa and −70 kDa diluted in Hanks') were analyzed with use of Cytofluor microplate reader. The filters used were 485 nm (excitation, band width 20 nm) and 530 nm (emission, band width 25 nm). The standard curves were made from both types of fluorescent dextrans with five parallels in the range 0 mg/ml to 0.01 mg/ml. The fitting curves gave correlation coefficients $R^2$=0.998 and $R^2$=0.979 for 10 kDa and 70 kDa respectively.

Samples were collected 5-, 15-, 30-, 45-, 60-, 90-, 120- and 150 minutes after the discs were transferred into Hanks' solution. After 150 minutes the measured values reached a plateau. With use of non-linear fit curves described by $f(t)=100-100e^{-kt}$ (k: rate constant, t: time), and calculation programs in GraFit Workspace were the half times determined. The results are presented in table 13.

TABLE 13

Solutions added alginate foam discs (V = 80 µl/disc, n = 3).

| Solution no. | Alginate concentration, [%] | Fluorescent dextran, molecular weight, [kDa] | Half time, [min] ± SD |
|---|---|---|---|
| 1 | 1.0 | 10 | 16.9 ± 1.3 |
| 2 | 0.5 | 10 | 15.4 ± 1.3 |
| 3 | 1.0 | 70 | 22.0 ± 1.3 |
| 4 | 0.5 | 70 | 21.2 ± 1.5 |

The results show a significant difference in release rate between the two molecular weights of fluorescent dextran. The results also indicate a faster release of both dextrans immobilized in lower concentrations of alginate.

EXAMPLE 9

This example show immobilization of cells into alginate foams and the use of peptide coupled alginates to promote cell proliferation.

The alginate foam used in this example was added calcium sufficient to saturate 125% of the alginate. The wet foam formulation is presented in table 14.

TABLE 14

Wet foam formulation.

| Ingredient | Amount, [g] |
|---|---|
| 4% alginate solution (PRONOVA UP MVG, FP-311-01) | 106.8 |
| Glycerin | 6.0 |
| Sorbitol (dry) | 13.9 |
| HPMC | 3.0 |
| $CaCO_3$ (HuberCal 500 Elite) | 0.85 |
| GDL | 3.01 |
| MQ-water | 66.4 |
| Total | 200.0 |

The foam was made as described in Example 1, except that the wet density was 0.24 g/ml and the foam was cast in a 2 mm high mold coated with Teflon. The equipment used were either depyrogenized by heat treatment at 250° C. for 4 hours or washed in 1 M NaOH. The dried foam was sterilized by gamma-irradiation (dose: 29.5 kGy).

Sterile foam disks (diameter=2.1 cm) were stamped out with use of a cork borer and transferred to wells in a 12 well plate. Table 15 presents three different blends of cells ($C_2C_{12}$) and alginate that were prepared. The cells were suspended in growth medium (DMEM) and quantified with use of a Bürker cell counting chamber. Regular alginate (PRONOVA SLG 20, batch: 221105) was dissolved in DMEM, whereas peptide coupled alginates (NOVATACH VAPG and NOVATACH RGD) were dissolved in 250 mM mannitol. The densities of peptide coupled to the alginates were measured to be 0.045 µmole/mg solid and 0.031 µmole/mg solid for NOVATACH VAPG and NOVATACH RGD respectively (measured by amino acid method).

TABLE 15

Suspensions for immobilization of cells.

| Material | Suspension 1 [ml] | Suspension 2 [ml] | Suspension 3 [ml] |
|---|---|---|---|
| Cells (1 056 667 cells/ml) | 0.43 | 0.43 | 0.43 |
| Alginate solution (2%, w/v) | 2.25 | 1.75 | 1.53 |
| DMEM | 1.82 | 1.33 | 1.10 |
| NOVATACH VAPG (1%, w/v) | — | 1.00 | — |
| NOVATACH RGD (1%, w/v) | — | — | 1.45 |
| Total | 4.50 | 4.50 | 4.50 |

Each suspension has a total alginate concentration of 1.0%. 250 µl of the suspensions presented in table 15 was added each foam disk, different suspensions to different disks. The calcium in the foam is sufficient to saturate the G monomers in the total amount of alginate with 77%. The peptide concentration in each disk was 0.025 µmole and amount of cells was 25 000 per disk. The suspension was dripped onto the foam with use of a pipette. The foam absorbed all the added solution and the thickness after hydration was about 1.2 mm. The foams were after addition of cell suspension transferred to an incubator and kept at 37° C. for 20 minutes. Then half of the foam disks were added about 2.5 ml DMEM whereas the other half were added about 2.5 ml of an isotonic solution of 50 mM $CaCl_2$ and 250 mM mannitol. After about five minutes the foams added the calcium containing solution got this solution replaced with DMEM.

After two days the cells were isolated as described in Example 5, except that the foam disks were dissolved in a solution containing 50 mM trisodiumcitrate and 250 mM mannitol. The pellets of cells after centrifugation were resuspended in 600 µl 250 mM mannitol. Three samples of each of 100 µl and 80 µl of the re-suspended pellets were then transferred to wells in a 96 wells plate. Then zero and 20 µl of mannitol respectively were added (i.e., to fill each well to a total of 100 µl) and then a further 100 µl of live/dead reagent. The live/dead reagent was made from 5 ml mannitol solution (250 mM), 20 µl ethidium solution (2 mM) and 5 µl calcein solution (4 mM). Standard curves were prepared from viable and ethanol fixed cells within the range of 0-$10^5$ cells. The fitting curves gave correlation coefficients $R^2$=0.988 and $R^2$=0.984 for viable and dead cells respectively.

The quantification of viable cells isolated from each foam disk was performed with use of Cytofluor microplate reader as described in Example 5. The results are presented in table 16. The signals for dead cells were about the blank value for all samples so these data are not shown.

TABLE 16

Cell viability and proliferation as a function of time for the different composites. (n = 3, ± SEM)

| Foam | Calcium wash after cell immobilization | Viable cells |
|---|---|---|
| Suspension 1 | No | 19 400 ± 1 300 |
| Suspension 1 | Yes | 20 200 ± 980 |
| Suspension 2 | No | 31 200 ± 1 900 |
| Suspension 2 | Yes | 20 100 ± 1 000 |
| Suspension 3 | No | 60 800 ± 1 000 |
| Suspension 3 | Yes | 46 300 ± 500 |

The data in table 16 indicate that NOVATACH RGD promote cell proliferation most

EXAMPLE 10

This example presents a method for producing chitosan foams and their characteristics related to density and absorption.

An aqueous solution containing 4% chitosan salt was prepared using PROTASAN CL 210 (214). 77.0 g MQ-water and 14.0 g sorbitol (dry) were added a mixing bowl and the sorbitol were dissolved by gently swirling the bowl. 100 g of the chitosan solution, 6.0 g glycerin and 3.0 g HPMC were added to the same mixing bowl. The dispersion was blended with a Hobart kitchen aid mixer equipped with a wire whisk at medium speed for one minute to ensure homogeneity. The mixing continued at high speed for 2.5 minutes. The wet density was measured to be 0.23 g/ml (determined from the weight of wet foam required to fill a 100 ml container). The wet foam was cast in 2 mm and 4 mm high molds coated with Teflon and then placed in a drying oven at 80° C. for 30 minutes and 60 minutes, respectively.

Another foam was made by the procedure as above, but the wet foam was molded in a 8 mm deep mold. The foam was dried at 80° C. for 1 hour and then 3 hours at 40° C.

The resulting dry foams were flexible and soft with an open pore network. When water was added to the foam it was immediately absorbed and the foam expanded significantly. The hydrated foam retained its shape, but was relatively weak in that the wet foam could not be transferred in one piece by lifting it from one corner. Compressing the dry foam before hydration did not noticeably affect the foam's absorbency rate or absorption capacity.

To measure the absorption capacity foam pieces were cut at 3.5 cm by 3.5 cm with use of a scalpel. A foam piece was weighted and placed on a mesh (diameter 0.71 mm) and Hanks' Balanced Salt Solution, as a model physiological solution, was added using a pipette. Excess liquid was added and the foams turned transparent. When no dripping from the foam piece was observed, the weight of the wet foam was measured. The dry density and the absorption capacity for the three different foams were measured, and the results are presented in table 17

TABLE 17

Dry density and absorption capacity of a model physiological solution of chitosan foams of different thickness (n = 3, ± SD).

| Thickness foam before drying, [mm] | Thickness dry foam, [mm] | Weight dry foam, 3.5 cm by 3.5 cm, [g] | Dry density, [g/cm³] | Weight wet foam, [g] | Absorption, [g Hanks' absorbed/g foam] |
|---|---|---|---|---|---|
| 2 | 1.95 | 0.101 ± 0.002 | 0.042 ± 0.001 | 2.02 ± 0.04 | 19.0 ± 0.1 |
| 4 | 3.20 | 0.164 ± 0.003 | 0.042 ± 0.001 | 3.20 ± 0.12 | 18.5 ± 0.8 |
| 8 | 5.50 | 0.390 ± 0.013 | 0.058 ± 0.002 | 6.76 ± 0.12 | 16.4 ± 0.3 |

EXAMPLE 11

This example presents a two-layer foam material made comprising alginate foam as the first layer and chitosan foam as a second layer attached to the alginate foam. This type of composite may be used to modify integrity, strength, biodegradation and absorption capacity of the chitosan foam.

An alginate foam was made by first preparing an aqueous solution containing 4% alginate (PRONOVA UP MVG). 111.2 g of the alginate solution was transferred to a mixing bowl. To the same bowl 6.0 g glycerin, 18.0 g sorbitol special, 3.0 g HPMC, 0.85 g $CaCO_3$ (sufficient to saturate the guluronic residues in the alginate with 125%) and 33.3 g MQ-water were added. The dispersion was blended with a Hobart kitchen aid mixer equipped with a wire whisk at medium speed for 1 minute and 30 seconds to ensure homogeneity. The mixing continued at high speed for 7 minutes before a freshly mixed GDL solution of 2.69 g GDL and 25.0 g MQ-water was added. The mixing continued at high speed for 1 minute, which resulted in a foam with a wet density of 0.23 g/ml. The wet foam was cast in 4 mm and 2 mm high molds coated with Versi-Dry bench protector with the polyethylene side towards the foam (Nalgene Nunc International, NY, USA) and kept uncovered for 60 minutes at room temperature.

Then wet chitosan foam was added on top of the gelled wet alginate foams as layers of 2 mm and 4 mm (by increasing the mold height) to the top of the 2 mm and 4 mm thick gelled alginate foams, respectively. The chitosan foam was made as described in Example 10 except 18.0 g sorbitol special was used in place of dry sorbitol and 73.0 g MQ-water was added for this foam. The mixing time at medium speed was 2 minutes and then 3 minutes of high speed mixing, which resulted in a foam with a wet density of 0.22 g/ml. The molds with the two-layered foams were then placed in a drying oven at 80° C. for 1.5 hours before it was transferred to an oven at 37° C. and the drying continued overnight.

The resulting dry foams were soft and flexible with an open pore network. The pores in the alginate foam part were smaller than in the foam made from chitosan. It was not possible to separate the two foam types after drying. Each foam layers absorbed water instantly (the absorption time of the first added drop was less than 1 second for the chitosan foam and about 3 seconds for the alginate foam) and they remained attached after hydration. The hydrated alginate part of the hydrated foam had a high tensile strength whereas the hydrated chitosan part was very weak. Pieces of the hydrated chitosan foam broke off when a finger was pushed against the chitosan foam side or when the chitosan foam was stretched by pushing against the reverse (alginate foam) side. The failure was not delamination.

EXAMPLE 12

This example describes a method for cross-linking a chitosan foam for making it more stable related to biodegradation and providing higher wet integrity.

A chitosan foam was made as described in example 11 except that the mixing times were 1.5 minutes and 4.5 minutes at medium and high speed respectively. The resulting wet foam density was 0.20 g/ml. The wet foam was cast in 2 mm and 4 mm deep molds. Then a 100 mM solution of Na-triphosphate filled in a spray bottle with the nozzle adjusted to give fine droplets. The Na-triphosphate solution was sprayed onto the wet foams about 50 ml and 100 ml for the 2 mm and the 4 mm respectively. The wet foams absorbed some of the solution sprayed on, so the addition was performed several times with less than a minute between each addition. The wet foams were then dried in a drying oven at 80° C. for 1 hour and 2 hours for the foams cast in the 2 mm and 4 mm molds respectively.

The dry foams were soft, flexible and had an open pore network. The foams absorbed water instantly and they deformed less upon hydration and were stronger than the non-crosslinked chitosan foams in Example 10.

EXAMPLE 13

This example shows that a chitosan foam containing gelling ions will have the ability to induce gelling of an externally added chitosan solution in situ.

Foam disks (diameter=2.1 cm) were stamped out with use of a cork borer from the foam cast in the 4 mm high mold presented in Example 12. A foam disk was then placed on the serrated plate on the same rheometer as used in previous example. The disk was then added excess solution of either MQ-water or a 1.0% solution of chitosan (PROTASAN UP CL 213). The upper plate (PP25) was lowered to a gap of 500 µm and a stress sweep was performed with an applied shear stress from 0.5 Pa to 50 Pa. The oscillation measurements were initiated about three minutes after addition of solution. The frequency was set to 1 Hz. The sweep was performed two times for each foam patch. The elastic modulus, G', read in the linear viscoelastic region ($G'_{lin}$) and the phase angle are reported in Table 18.

TABLE 18

G'$_{lin}$ and phase angle measured for cross linked
chitosan foams added water and chitosan solution.

| Solution added | G'$_{lin}$ ± SD, [Pa] | Phase angle, [°] |
|---|---|---|
| MQ-water | 502 ± 65 | 24.6 ± 0.3 |
| 1.0% chitosan solution | 777 ± 29 | 17.6 ± 4.1 |

Based on both the elastic modulus and the phase angle indicate the results in the table a more gel like properties of the foam after addition of chitosan solution.

EXAMPLE 14

This example shows how the mixing time and amount of air incorporated into the chitosan foams affects different foam properties.

Chitosan foams were prepared as described in Example 10 except different mixing times were used to obtain different foam densities. All foam ingredients for creating a wet foam was mixed at medium speed for 1.5 minutes. Then mixing at high speed was continued for 1 minute with a resulting wet density 0.45 g/ml. About half of the foam was cast in 4 mm and 2 mm high molds. Then the remaining foam was mixed at high speed for one additional minute. The resulting wet density was 0.29 g/ml and the rest of the foam was cast as above. A similar procedure as above was repeated except for the mixing times at high speed were first 45 seconds and the second 4 minutes and 45 seconds. The wet densities were 0.52 g/ml and 0.18 g/ml respectively. The two foams with highest wet densities got a thin film created at the surface against the mold. This is due to coalescence of the pores as the foam dries more slowly near the bottom. The dry foam density was determined by stamping out disks, from the foam cast in the 4 mm high mold, with a diameter of 1 cm with use of a cork borer and weighing them. The densities and thickness measured by a caliper of the different foams are presented in table 18. The foams were also characterized by its elastic modulus, G'$_{lin}$, with the same rheometer settings as described in Example 10 except the range of applied stress was 0.5 Pa to 18 Pa, and that three sweeps for each foam piece were performed. The results are included in table 19, presenting the average values of the two last sweeps for three different foams with a diameter of 1 cm. The foam pieces were kept in 2 ml Hanks' solution about five minutes before they were transferred to the rheometer. The tensile strength of the dried foams was measured with use of a SMS Texture Analyzer and A/TG tensile grips. The force required stretching the foam at 0.5 mm/s until breakage was read and maximum force and distance stretched when it ruptured are reported in table 19. The foam pieces were bone-shaped cut with use of a scalpel with the dimensions; 3.15 cm long, 1.75 cm wide at the ends and 1.25 cm wide in the center, the narrowing start 1 cm from the ends. The foam was cut in this shape to ensure breakage in the middle of the foam and not where it was attached to the grips. Approximate 0.3 cm of each end of the foam piece was used to fasten it to the grips.

TABLE 19

Chitosan foams of different density and their properties.
(n = 3, ± SEM) (The foam with wet density of
0.23 g/ml is the foam from Example 10)

| Foam wet density, [g/ml] | Foam dry density, [mg/cm²] | Thickness, [mm] | Tensile strength, [g] | Distance before rupture, [mm] | G'$_{lin}$, [Pa] |
|---|---|---|---|---|---|
| 0.52 | 24.8 ± 0.2 | 2.4 | 138 ± 10 | 20 ± 2 | 133 ± 23 |
| 0.45 | 22.4 ± 0.7 | 2.5 | 148 ± 8 | 14 ± 2 | 115 ± 6 |
| 0.29 | 17.4 ± 0.4 | 3.2 | 79 ± 1 | 5.1 ± 0.2 | 55 ± 3 |
| 0.23 | 15.4 ± 0.2 | 3.4 | 60 ± 1 | 6.6 ± 0.3 | 51 ± 1 |
| 0.18 | 12.5 ± 0.3 | 3.7 | 49 ± 1 | 6.7 ± 0.5 | 9 ± 1 |

The table shows that the foams with the highest wet densities collapsed most due to coalescence. It was also observed that the foams had increasing pore size by increasing wet density. The tensile strength and the elastic modulus decreased by increased amounts of air. Also the elasticity of the materials presented as the length the material could be stretched before it ruptured decreased by decreasing wet density. The three less dense materials had about the same elasticity.

EXAMPLE 15

This example describes the preparation of a hyaluronic acid (HA) foam with calcium ions incorporated. Also the foams ability to donate these ions to induce gelling of an externally added alginate solution is shown.

An aqueous solution containing 2.5% HA was prepared and set aside. 49.65 g MQ-water, 2.35 g CaCl$_2$*2H$_2$O and 10.5 g sorbitol (dry) were added a mixing bowl and the dry ingredients were dissolved by gently swirling the bowl. 130 g of the HA solution, 4.5 g glycerin and 3.0 g HPMC were added to the same mixing bowl. The dispersion was then blended with a Hobart kitchen aid mixer equipped with a wire whisk at medium speed for two minutes to ensure homogeneity. The mixing continued at high speed for 3 minutes and 50 seconds. The wet density was measured to be 0.21 g/ml (determined from the weight of wet foam required to fill a 100 ml container). The wet foam was cast in 2 mm and 4 mm high molds coated with Teflon and then placed in a drying oven at 80° C. for 50 minutes.

With use of a cork borer foam disks (diameter=2.1 cm) were stamped out from the foam cast in the 4 mm high mold. A 1.0% and 0.5% alginate solution was prepared from PRONOVA SLG 20 (batch: 221105) by addition of MQ-water. A dry foam disk was placed on a Bohlin CVO 120 High Resolution Rheometer between serrated plates (PP25). Then 350 µl of the alginate solution was added with use of a pipette. The calcium content in the foam disk is enough to saturate gelling residues of the added alginate by 124% and 248% for the 1.0% and 0.5% solution respectively. After one minute the alginate solution is absorbed and the foam is close to be fully hydrated. The upper plate was then lowered to 500 µm gap and measurements of the elastic modulus, G', was initiated. The frequency, strain and temperature were set to 1 Hz, 0.001 and 20° C. respectively. The results are presented in table 20.

TABLE 20

Elastic modulus, G', as a function of time after addition of water and alginate solutions to the HA foam with calcium ions incorporated.

| | Elastic modulus, G', [Pa] | | |
|---|---|---|---|
| Time, [min] | MQ-water | 0.5% alginate | 1.0% alginate |
| 2 | 26 | 743 | 1665 |
| 4 | 31 | 660 | 2153 |
| 6 | 27 | 698 | 2544 |
| 8 | 25 | 750 | 3003 |
| 10 | 25 | 816 | 3322 |
| 15 | — | 1003 | 4167 |
| 20 | — | 1193 | 4732 |
| 25 | — | 1355 | 5608 |
| 30 | — | 1591 | 6292 |
| 35 | — | 1867 | 6602 |

The increase of G' during the minutes just after addition of the alginate solution, confirms donation of gelling ions and that a gelling reaction have been initiated. The difference in G' value between the three solutions confirms that a gel is being created and that the strongest gel is created from the most concentrated alginate solution.

EXAMPLE 16

This example describes the preparation of a HA foam with phosphate ions incorporated. Also the foams ability to donate these ions to induce gelling of an externally added chitosan solution is shown.

The HA foam was made as described in Example 15, except that the calcium source was replaced with 2.27 g $Na_2HPO_4$ and the amount of water used was 49.7 g. The mixing time at high speed was 3 minutes with gave a wet density of 0.17 g/ml. The foams cast in 2 mm and 4 mm molds were kept in the drying oven at 80° C. for 45 min and 75 min respectively.

The same parameters for rheological measurements as described in Example A were used. Water and 1.0% chitosan solution was added in excess amount. The values describing the elastic modulus, G', and phase angle flattened off at the values presented in table 21.

TABLE 21

Elastic modulus, G', and phase angle of rehydrated HA foams with phosphate ions incorporated.

| Solution added | Elastic modulus, G', [Pa] | Phase angle, [°] |
|---|---|---|
| 1% chitosan solution | 76 | 22 |
| MQ-water | 18 | 46 |

The results indicate that the foam added chitosan solution gets a more gel like behavior and is stiffer than the foam added MQ-water.

EXAMPLE 17

This example describes the preparation of a chitosan foam that contains calcium ions. The calcium immobilized in the chitosan foam induced in situ gelling of an alginate solution when it was absorbed by the dry chitosan foam. Such structures may be useful in biomedical applications for cell immobilization or to provide controlled release of immobilized drugs, enzymes, hormones, etc.

A chitosan foam was made comprising the same amounts and ingredients as in example 11 except that 2.35 g of MQ-water were replaced with 2.35 g $CaCl_2 \cdot 2H_2O$ (80 mM). A wet foam with a wet density of 0.20 g/ml were made by mixing at medium and high speed for 1.5 minutes and 6 minutes respectively. The wet foam was cast in 2 mm and 4 mm high molds as described earlier. Then they were placed in a drying oven at 80° C. for 1.5 hours. The dry foams were soft and flexible with an open pore network and a dry density of 0.039±0.001 g/cm³. The foam absorbed water instantly and had wet integrity similar to the foams of same thickness in Example 10. This foam expanded less when Hanks' solution was added this foam compared with the foams from Example 10. The absorption capacity of Hanks' solution for this foam was measured to be 16.8±1.9 g/g foam (average value of three samples SD). The pores of this foam were somewhat larger than the 4 mm thick foam from Example 10, this may be described by more coalescence due to decreased viscosity of the chitosan because of the ionic strength of the solution.

Foam discs, from the foam molded in 4 mm high trays, were stamped out with use of a cork borer with a diameter of 2.1 cm. A dry foam disc was the placed on a Bohlin CVO 120 High Resolution Rheometer between serrated plates (PP25). Then 500 µl of a 1% alginate (PRONOVA UP LVG) solution was added with use of a pipette. The calcium content in the foam disc is enough to saturate gelling residues of the added alginate by 96%. After one minute the alginate solution is absorbed and the foam is close to be fully hydrated. The upper plate was lowered to 1.000 mm gap and measurements of the elastic modulus, G', were initiated. The frequency, strain and temperature were set to 1 Hz, 0.001 and 20° C. respectively. The results are presented in table 22.

TABLE 22

The elastic modulus, G', as a function of time for chitosan foams added alginate solution and water (n = 3).

| Time, [min] | Elastic modulus, G' ± SD [Pa] (alginate) | Elastic modulus, G', ± SD [Pa] (water) |
|---|---|---|
| 1 | 4987 ± 5 | 470 ± 16 |
| 2 | 5867 ± 40 | 501 ± 13 |
| 3 | 6346 ± 15 | 516 ± 15 |
| 4 | 6653 ± 72 | 515 ± 9 |
| 5 | 6850 ± 64 | 529 ± 17 |
| 7 | 7078 ± 65 | 531 ± 23 |
| 9 | 7191 ± 76 | 532 ± 23 |
| 11 | 7216 ± 122 | 536 ± 21 |
| 12 | 7260 ± 120 | 534 ± 21 |

The high value of G' for the foam discs added alginate solution and the increase in G' during the minutes just after addition, confirms donation of gel-forming ions to the added alginate solution from the chitosan foam.

The invention claimed is:
1. A composite comprising a foam comprising alginate and a polysaccharide gel comprising alginate and cells within the pores of said foam, wherein said polysaccharide gel is chemically bonded to said foam, said composite prepared by a process comprising contacting:
(i) a foam comprising (a) a polymer comprising alginate and (b) gel-forming ions capable of forming a gel with a liquid component comprising a polysaccharide comprising alginate, with
(ii) a liquid component comprising a soluble polysaccharide comprising alginate and cells, whereby upon con- tact of said alginate in said liquid component with said gel-forming ions, a polysaccharide gel comprising alginate and cells is formed within the pores of said foam and is chemically bonded to said foam to form said composite.

2. The composite according to claim to 1, wherein the foam absorbs from 1 to 30 times its weight of the liquid component.

3. The composite according to claim 1 wherein the elastic modulus of the composite is from 0.1 kPa to 1000 kPa.

4. The composite according to claim 1 in which the foam and/or the polysaccharide comprises an ultrapure polysaccharide possessing a low content of endotoxins.

5. The composite for inhibiting cell proliferation comprising the composite according to claim 1, wherein the gel-forming ion comprises barium ion, strontium ion, or mixtures thereof.

6. The composite for promoting cell proliferation comprising the composite according to claim 1, wherein the gel-forming ion comprises calcium ion.

7. The composite according to claim 1, wherein the gel-forming ions comprise at least one of calcium ions, strontium ions and barium ions, and the gelling ions are present in a molar amount equivalent to 5% to 200% of the gelling sites of the soluble polysaccharide.

\* \* \* \* \*